(12) United States Patent
Haack et al.

(10) Patent No.: US 11,046,743 B2
(45) Date of Patent: Jun. 29, 2021

(54) SELECTIVE GLUCAGON RECEPTOR AGONISTS COMPRISING A CHELATING MOIETY FOR IMAGING PURPOSES

(71) Applicant: Antaros Medical AB, Mölndal (SE)

(72) Inventors: Torsten Haack, Frankfurt am Main (DE); Oliver Plettenburg, Frankfurt am Main (DE); Andreas Evers, Frankfurt am Main (DE); Michael Wagner, Frankfurt am Main (DE); Martin Bossart, Frankfurt am Main (DE); Romain Bertrand, Frankfurt am Main (DE)

(73) Assignee: ANTAROS MEDICAL AB, Mölndal (SE)

( * ) Notice: Subject to any disclaimer, the term of this patent is extended or adjusted under 35 U.S.C. 154(b) by 278 days.

(21) Appl. No.: 16/061,421

(22) PCT Filed: Dec. 12, 2016

(86) PCT No.: PCT/EP2016/080553
§ 371 (c)(1),
(2) Date: Jun. 12, 2018

(87) PCT Pub. No.: WO2017/102613
PCT Pub. Date: Jun. 22, 2017

(65) Prior Publication Data
US 2020/0262885 A1 Aug. 20, 2020

(30) Foreign Application Priority Data
Dec. 14, 2015 (EP) .................................... 15307000

(51) Int. Cl.
| C07K 14/605 | (2006.01) |
| A61P 3/10 | (2006.01) |
| C07K 14/575 | (2006.01) |
| A61K 38/00 | (2006.01) |

(52) U.S. Cl.
CPC ............. *C07K 14/605* (2013.01); *A61P 3/10* (2018.01); *C07K 14/57563* (2013.01); *A61K 38/00* (2013.01)

(58) Field of Classification Search
CPC ... C07K 14/605; C07K 14/57563; A61P 3/10; A61P 3/08; A61P 3/00; A61K 38/00; A61K 38/28; A61K 45/06
See application file for complete search history.

(56) References Cited

U.S. PATENT DOCUMENTS

| 8,268,781 B2 | 9/2012 | Gotthardt et al. |
| 2015/0368311 A1* | 12/2015 | Haack .................... A61P 39/02 514/5.3 |

FOREIGN PATENT DOCUMENTS

| WO | 2006024275 A2 | 3/2006 |
| WO | 2006127948 A2 | 11/2006 |
| WO | WO 2007140284 A2 | 12/2007 |
| WO | WO 2014096145 A1 | 6/2014 |
| WO | 2015193381 A1 | 12/2015 |

OTHER PUBLICATIONS

Eng et al. (1992) "Isolation and Characterization of Exendin-4, an Exendin-3 Analogue, from Heloderma suspectum Venom," The Journal of Biological Chemistry, 267(11):7402-7406.
Eriksson et al. (2014) "Detection of Metastatic Insulinoma by Positron Emission Tomography With [68Ga]Exendin-4—A Case Report," J. Clin. Endocrinol Metab., 99(5):1519-1524.
King et al. (1990) "A cleavage method which minimizes side reactions following Fmoc solid phase peptide synthesis," Int. J. Peptide Protein Res., 36, pp. 255-266.
Selvaraju et al. (2013) "In Vivo Imaging of the Glucagonlike Peptide 1 Receptor in the Pancreas with 68Ga-Labeled DO3A-Exendin-4," The Journal of Nuclear Medicine, 54(8):1458-1463.
Unson et al. (1993) "The Role of Histidine-1 in Glucagon Action," Archives of Biochemistry and Biophysics, 300 (2):747-750.
Wadas et al. (2010) "Coordinating Radiometals of Copper, Gallium, Indium, Yttrium, and Zirconium for PET and SPECT Imaging of Disease," Chem. Rev., 110(5):2858-2902.
Watanabe et al. (1998) "Histologic distribution of insulin and glucagon receptors," Brazilian Journal of Medical and Biological Research, 31(2):243-256.
European Search Report corresponding to European Patent Application No. 15307000, dated Feb. 19, 2016.
International Search Report corresponding to International Application No. PCT/EP2016/080553, dated Feb. 7, 2017.

* cited by examiner

*Primary Examiner* — Sudhakar Katakam
(74) *Attorney, Agent, or Firm* — Lathrop GPM LLP; James H. Velema, Esq.

(57) ABSTRACT

The present invention relates to exendin-4 peptide analogues which selectively bind and activate the glucagon receptor and comprise a chelating moiety capable of binding a metal ion and their use, for example in PET imaging.

20 Claims, No Drawings
Specification includes a Sequence Listing.

SEQUENCE LISTING

<160> NUMBER OF SEQ ID NOS: 91

<210> SEQ ID NO 1
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: Amidated C-terminus

<400> SEQUENCE: 1

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 2
<211> LENGTH: 29
<212> TYPE: PRT
<213> ORGANISM: Homo sapiens

<400> SEQUENCE: 2

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr
            20                  25

<210> SEQ ID NO 3
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2,5-dioxo-1-{2-[2-(4,7,10-tris-carboxymethyl-1,4,7,10-tetraaza-
      cyclododec-1-yl)-acetylamino]-ethyl}-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 3

Xaa Ser Gln Gly Thr Phe Thr Ser Asp Tyr Ser Lys Gln Leu Glu Ser
 1               5                  10                  15

Arg Arg Ala Gln Glu Phe Ile Glu Trp Leu Leu Ala Gly Gly Pro Glu
            20                  25                  30

Ser Gly Ala Pro Pro Ser Xaa
        35                  40

<210> SEQ ID NO 4
<211> LENGTH: 40
<212> TYPE: PRT
<213> ORGANISM: Artificial Sequence
<220> FEATURE:
<223> OTHER INFORMATION: artificial polypeptide

```
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      1-{2-[2-(4,7-bis-carboxymethyl-[1,4,7]triazonan-
      1-yl)-acetylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 4

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 5
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with 1-{2-[(S)-4-(4,7-
      bis-carboxymethyl-[1,4,7]triazonan-
      1-yl)-4-carboxy-butyrylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 5

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 6
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
```

```
<220> FEATURE:
<221> NAME/KEY: MOD_RES
<222> LOCATION: (40)..(40)
<223> OTHER INFORMATION: Amidated C-terminus

<400> SEQUENCE: 6

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 7
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
     2,5-dioxo-1-{2-[2-(4,7,10-tris-carboxymethyl-1,4,7,10-tetraaza-
     cyclododec-1-yl)-acetylamino]-ethyl}-pyrrolidin-3-yl with
     complexed Gallium
<220> FEATURE:
<221> NAME/KEY: MOD_RES
<222> LOCATION: (40)..(40)
<223> OTHER INFORMATION: Amidated C-terminus

<400> SEQUENCE: 7

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 8
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
     2-[2-(4,7,10-Tris-carboxymethyl-1,4,7,10-tetraaza-cyclododec-1-
     yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus
```

```
<400> SEQUENCE: 8

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
            35                  40

<210> SEQ ID NO 9
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      1-{2-[2-(4,7-bis-carboxymethyl-[1,4,7]triazonan-
      1-yl)-acetylamino]ethyl}-2,5-dioxo-pyrrolidin-3-yl with
      complexed Gallium
<220> FEATURE:
<221> NAME/KEY: MOD_RES
<222> LOCATION: (40)..(40)
<223> OTHER INFORMATION: Amidated C-terminus

<400> SEQUENCE: 9

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
            35                  40

<210> SEQ ID NO 10
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with 1-{2-[(S)-4-(4,7-
      bis-carboxymethyl-[1,4,7]triazonan-
      1-yl)-4-carboxy-butyrylamino]ethyl}-2,5-dioxo-pyrrolidin-3-yl
      with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 10

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
            35                  40
```

-continued

```
<210> SEQ ID NO 11
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-tert-Leucine (Tle)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (28)..(28)
<223> OTHER INFORMATION: Xaa is beta-Alanine (Bal)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 11

Xaa Ser Gln Gly Thr Phe Thr Ser Asp Xaa Ser Lys Gln Xaa Glu Ser
1               5                   10                  15

Arg Arg Ala Gln Glu Phe Ile Glu Trp Leu Leu Xaa Gly Gly Pro Glu
            20                  25                  30

Ser Gly Ala Pro Pro Pro Ser Xaa
        35                  40

<210> SEQ ID NO 12
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-tert-Leucine (Tle)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (28)..(28)
<223> OTHER INFORMATION: Xaa is beta-Alanine (Bal)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus
```

```
<400> SEQUENCE: 12

Xaa Ser Gln Gly Thr Phe Thr Ser Asp Xaa Ser Lys Gln Xaa Glu Ser
1               5                   10                  15

Arg Arg Ala Gln Glu Phe Ile Glu Trp Leu Leu Xaa Gly Gly Pro Glu
            20                  25                  30

Ser Gly Ala Pro Pro Pro Ser Xaa
        35                  40

<210> SEQ ID NO 13
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 13

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 14
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
```

<220> FEATURE:
<221> NAME/KEY: MOD_RES
<222> LOCATION: (40)..(40)
<223> OTHER INFORMATION: Amidated C-terminus

<400> SEQUENCE: 14

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 15
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
    2,5-dioxo-1-{2-[2-(4,7,10-tris-carboxymethyl-1,4,7,10-tetraaza-
    cyclododec-1-yl)-acetylamino]-ethyl}-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 15

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 16
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)

-continued

```
<220> FEATURE:
<221> NAME/KEY: MOD_RES
<222> LOCATION: (40)..(40)
<223> OTHER INFORMATION: Xaa is Cys derivatized with
      1-{2-[2-(4,7-bis-carboxymethyl-[1,4,7]triazonan-
      1-yl)-acetylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 16

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 17
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with 1-{2-[(S)-4-(4,7-
      bis-carboxymethyl-[1,4,7]triazonan-
      1-yl)-4-carboxy-butyrylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 17

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 18
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
```

```
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2,5-dioxo-1-{2-[2-(4,7,10-tris-carboxymethyl-1,4,7,10-tetraaza-
      cyclododec-1-yl)-acetylamino]-ethyl}-pyrrolidin-3-yl with
      complexed Gallium
<220> FEATURE:
<221> NAME/KEY: MOD_RES
<222> LOCATION: (40)..(40)
<223> OTHER INFORMATION: Amidated C-terminus

<400> SEQUENCE: 18

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 19
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      1-{2-[2-(4,7-bis-carboxymethyl-[1,4,7]triazonan-
      1-yl)-acetylamino]ethyl}-2,5-dioxo-pyrrolidin-3-yl with
      complexed Gallium
<220> FEATURE:
<221> NAME/KEY: MOD_RES
<222> LOCATION: (40)..(40)
<223> OTHER INFORMATION: Amidated C-terminus

<400> SEQUENCE: 19

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 20
<211> LENGTH: 40
<212> TYPE: PRT
<213> ORGANISM: Artificial Sequence
<220> FEATURE:
<223> OTHER INFORMATION: artificial polypeptide
```

-continued

```
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with 1-{2-[(S)-4-(4,7-
      bis-carboxymethyl-[1,4,7]triazonan-
      1-yl)-4-carboxy-butyrylamino]ethyl}-2,5-dioxo-pyrrolidin-3-yl
      with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 20

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 21
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 21

Xaa Xaa Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 22
<211> LENGTH: 40
<212> TYPE: PRT
<213> ORGANISM: Artificial Sequence
<220> FEATURE:
<223> OTHER INFORMATION: artificial polypeptide
```

```
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 22

Xaa Xaa Gln Gly Thr Phe Thr Ser Asp Tyr Ser Lys Gln Leu Asp Ser
1               5                   10                  15

Arg Ala Ala Gln Asp Phe Ile Glu Trp Leu Leu Ala Gly Gly Pro Ser
            20                  25                  30

Ser Gly Ala Pro Pro Pro Ser Xaa
        35                  40

<210> SEQ ID NO 23
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 23

Xaa Xaa Gln Gly Thr Phe Thr Ser Asp Tyr Ser Lys Gln Leu Asp Ser
1               5                   10                  15

Arg Ala Ala Gln Asp Phe Ile Glu Trp Leu Leu Ala Gly Gly Pro Ser
            20                  25                  30

Ser Gly Ala Pro Pro Pro Ser Xaa
        35                  40

<210> SEQ ID NO 24
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
```

-continued

```
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 24

Xaa Xaa Gln Gly Thr Phe Thr Ser Asp Tyr Ser Lys Gln Leu Glu Ser
1               5                   10                  15

Gln Arg Ala Gln Asp Phe Ile Glu Trp Leu Leu Ala Gly Gly Pro Ser
            20                  25                  30

Ser Gly Ala Pro Pro Pro Ser Xaa
        35                  40

<210> SEQ ID NO 25
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 25

Xaa Xaa Gln Gly Thr Phe Thr Ser Asp Tyr Ser Lys Gln Leu Glu Ser
1               5                   10                  15

Gln Arg Ala Gln Asp Phe Ile Glu Trp Leu Leu Ala Gly Gly Pro Ser
            20                  25                  30

Ser Gly Ala Pro Pro Pro Ser Xaa
        35                  40

<210> SEQ ID NO 26
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
```

```
<220> FEATURE:
<221> NAME/KEY: MOD_RES
<222> LOCATION: (40)..(40)
<223> OTHER INFORMATION: Xaa is Lys derivatized with
      (4,7,10-Tris-carboxymethyl-1,4,7,10-tetraaza-cyclododec-1-yl)-
      acetyl
<220> FEATURE:
<221> NAME/KEY: MOD_RES
<222> LOCATION: (40)..(40)
<223> OTHER INFORMATION: Amidated C-terminus

<400> SEQUENCE: 26

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 27
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with
      (4,7,10-Tris-carboxymethyl-1,4,7,10-tetraaza-cyclododec-1-yl)-
      acetyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 27

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 28
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with
      (4,7-Bis-carboxymethyl-[1,4,7]triazonan-1-yl)-acetyl
<220> FEATURE:
<221> NAME/KEY: MOD_RES
<222> LOCATION: (40)..(40)
<223> OTHER INFORMATION: Amidated C-terminus
```

<400> SEQUENCE: 28

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
            35                  40

<210> SEQ ID NO 29
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with
      3-{2-[2-(2-{2-[3-(1-{2-[2-(4,7-Bis-carboxymethyl-[1,4,7]triazonan-
      1-yl)-acetylamino]-ethyl}-2,5-dioxo-pyrrolidin-3-ylsulfanyl)-
      propionylamino]-ethoxy}-ethoxy)-ethoxy]-ethoxy}-propionyl
<220> FEATURE:
<221> NAME/KEY: MOD_RES
<222> LOCATION: (40)..(40)
<223> OTHER INFORMATION: Amidated C-terminus

<400> SEQUENCE: 29

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
            35                  40

<210> SEQ ID NO 30
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with 3-{2-[2-(2-{2-[3-
      (1-{2-[2-(4,7-Bis-carboxymethyl-[1,4,7]triazonan-1-yl)-
      acetylamino]-ethyl}-2,5-dioxo-pyrrolidin-3-ylsulfanyl)-
      propionylamino]-ethoxy}-ethoxy)-ethoxy]-ethoxy}-propionyl with
      complexed Gallium
<220> FEATURE:
<221> NAME/KEY: MOD_RES
<222> LOCATION: (40)..(40)
<223> OTHER INFORMATION: Amidated C-terminus

<400> SEQUENCE: 30

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
            35                  40

<210> SEQ ID NO 31
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
    2-[2-(4,7,10-Tris-carboxymethyl-1,4,7,10-tetraaza-cyclododec-1-
    yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 31

Xaa Ser Gln Gly Thr Phe Xaa Ser Asp Leu Ala Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 32
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
    2-[2-(4,7,10-Tris-carboxymethyl-1,4,7,10-tetraaza-cyclododec-1-
    yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

```
<400> SEQUENCE: 32

Xaa Ser Gln Gly Thr Phe Xaa Ser Asp Leu Ala Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 33
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 33

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 34
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 34

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40
```

-continued

```
<210> SEQ ID NO 35
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 35

Xaa Ser Gln Gly Thr Phe Thr Ser Asp Ile Ser Lys Gln Xaa Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 36
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 36

Xaa Ser Gln Gly Thr Phe Thr Ser Asp Ile Ser Lys Gln Xaa Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 37
<211> LENGTH: 39
<212> TYPE: PRT
<213> ORGANISM: Artificial Sequence
```

```
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (12)..(12)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (39)..(39)
<223> OTHER INFORMATION: Amidated C-terminus

<400> SEQUENCE: 37

Xaa Ser Gln Gly Thr Phe Thr Ser Asp Tyr Ser Xaa Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser
        35

<210> SEQ ID NO 38
<211> LENGTH: 39
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (13)..(13)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (39)..(39)
<223> OTHER INFORMATION: Amidated C-terminus

<400> SEQUENCE: 38

Xaa Ser Gln Gly Thr Phe Thr Ser Asp Tyr Ser Lys Xaa Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser
        35

<210> SEQ ID NO 39
<211> LENGTH: 39
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
```

```
<220> FEATURE:
<221> NAME/KEY: MOD_RES
<222> LOCATION: (39)..(39)
<223> OTHER INFORMATION: Amidated C-terminus

<400> SEQUENCE: 39

Xaa Ser Gln Gly Thr Phe Thr Ser Asp Tyr Ser Lys Gln Xaa Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser
        35

<210> SEQ ID NO 40
<211> LENGTH: 39
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (16)..(16)
<223> OTHER INFORMATION: Xaa is Cys derivatized with
     2-[2-(4,7,10-Tris-carboxymethyl-1,4,7,10-tetraaza-cyclododec-1-
     yl)-ethanesulfonyl]-ethyl
<220> FEATURE:
<221> NAME/KEY: MOD_RES
<222> LOCATION: (39)..(39)
<223> OTHER INFORMATION: Amidated C-terminus

<400> SEQUENCE: 40

Xaa Ser Gln Gly Thr Phe Thr Ser Asp Tyr Ser Lys Gln Leu Glu Xaa
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (17)..(17)
<223> OTHER INFORMATION: Xaa is Cys derivatized with
     2-[2-(4,7,10-Tris-carboxymethyl-1,4,7,10-tetraaza-cyclododec-1-
     yl)-ethanesulfonyl]-ethyl
<220> FEATURE:
<221> NAME/KEY: MOD_RES
<222> LOCATION: (39)..(39)
<223> OTHER INFORMATION: Amidated C-terminus
```

```
<400> SEQUENCE: 41

Xaa Ser Gln Gly Thr Phe Thr Ser Asp Tyr Ser Lys Gln Leu Glu Ser
1               5                   10                  15

Xaa Arg Ala Gln Glu Phe Ile Glu Trp Leu Leu Ala Gly Gly Pro Glu
            20                  25                  30

Ser Gly Ala Pro Pro Pro Ser
        35

<210> SEQ ID NO 42
<211> LENGTH: 39
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (20)..(20)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (39)..(39)
<223> OTHER INFORMATION: Amidated C-terminus

<400> SEQUENCE: 42

Xaa Ser Gln Gly Thr Phe Thr Ser Asp Tyr Ser Lys Gln Leu Glu Ser
1               5                   10                  15

Arg Arg Ala Xaa Glu Phe Ile Glu Trp Leu Leu Ala Gly Gly Pro Glu
            20                  25                  30

Ser Gly Ala Pro Pro Pro Ser
        35

<210> SEQ ID NO 43
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 43

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40
```

```
<210> SEQ ID NO 44
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 44

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 45
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with
      (4,7,10-Tris-carboxymethyl-1,4,7,10-tetraaza-cyclododec-1-yl)-
      acetyl
<220> FEATURE:
<221> NAME/KEY: MOD_RES
<222> LOCATION: (40)..(40)
<223> OTHER INFORMATION: Amidated C-terminus

<400> SEQUENCE: 45

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 46
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
```

```
<220> FEATURE:
<221> NAME/KEY: MOD_RES
<222> LOCATION: (40)..(40)
<223> OTHER INFORMATION: Xaa is Lys derivatized with
      (4,7,10-Tris-carboxymethyl-1,4,7,10-tetraaza-cyclododec-1-yl)-
      acetyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 46

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 47
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 47

Xaa Ser Gln Gly Thr Phe Thr Ser Asp Thr Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 48
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus
```

```
<400> SEQUENCE: 48

Xaa Ser Gln Gly Thr Phe Thr Ser Asp Thr Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
            35                  40

<210> SEQ ID NO 49
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 49

Xaa Ser Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
            35                  40

<210> SEQ ID NO 50
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 50

Xaa Ser Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
            35                  40
```

```
<210> SEQ ID NO 51
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 51

Xaa Ser Gln Gly Thr Phe Xaa Ser Asp Leu Ser Lys Gln Xaa Glu Ser
1               5                   10                  15

Arg Arg Ala Lys Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 52
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus
```

<400> SEQUENCE: 52

Xaa Ser Gln Gly Thr Phe Xaa Ser Asp Leu Ser Lys Gln Xaa Glu Ser
1               5                   10                  15

Arg Arg Ala Lys Asp Phe Ile Glu Trp Leu Leu Ala Thr Gly Pro Glu
            20                  25                  30

Ser Gly Ala Pro Pro Pro Ser Xaa
            35                  40

<210> SEQ ID NO 53
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with
      (4,7-Bis-carboxymethyl-[1,4,7]triazonan-1-yl)-acetyl
<220> FEATURE:
<221> NAME/KEY: MOD_RES
<222> LOCATION: (40)..(40)
<223> OTHER INFORMATION: Amidated C-terminus

<400> SEQUENCE: 53

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
            35                  40

<210> SEQ ID NO 54
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (16)..(16)
<223> OTHER INFORMATION: Xaa is Aminoisobutyric acid (Aib)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 54

Xaa Ser Gln Gly Thr Phe Thr Ser Asp Tyr Ser Lys Gln Leu Glu Xaa
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
            35                  40

```
<210> SEQ ID NO 55
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (16)..(16)
<223> OTHER INFORMATION: Xaa is Aminoisobutyric acid (Aib)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 55

Xaa Ser Gln Gly Thr Phe Thr Ser Asp Tyr Ser Lys Gln Leu Glu Xaa
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 56
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (16)..(16)
<223> OTHER INFORMATION: Xaa is Aminoisobutyric acid (Aib)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 56

Xaa Ser His Gly Thr Phe Thr Ser Asp Tyr Ser Lys Gln Leu Glu Xaa
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 57
<211> LENGTH: 40
<212> TYPE: PRT
<213> ORGANISM: Artificial Sequence
```

```
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (16)..(16)
<223> OTHER INFORMATION: Xaa is Aminoisobutyric acid (Aib)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 57

Xaa Ser His Gly Thr Phe Thr Ser Asp Tyr Ser Lys Gln Leu Glu Xaa
1               5                   10                  15

Lys Lys Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 58
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (16)..(16)
<223> OTHER INFORMATION: Xaa is Aminoisobutyric acid (Aib)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 58

Xaa Xaa Gln Gly Thr Phe Thr Ser Asp Tyr Ser Lys Gln Leu Asp Xaa
1               5                   10                  15

Lys Lys Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 59
<211> LENGTH: 40
<212> TYPE: PRT
<213> ORGANISM: Artificial Sequence
```

```
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 59

Xaa Ser His Gly Thr Phe Thr Ser Asp Ile Ser Lys Gln Leu Asp Glu
 1               5                  10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 60
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (16)..(16)
<223> OTHER INFORMATION: Glu in position 16 forms a lactam bridge with
      Lys in position 20
<220> FEATURE:
<221> NAME/KEY: MOD_RES
<222> LOCATION: (20)..(20)
<223> OTHER INFORMATION: Lys in position 20 forms a lactam bridge with
      Glu in position 16
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 60

Xaa Xaa Gln Gly Thr Phe Thr Ser Asp Tyr Ser Lys Gln Leu Asp Glu
 1               5                  10                  15

Gln Arg Ala Lys Glu Phe Ile Glu Trp Leu Leu Ala Thr Gly Pro Glu
            20                  25                  30

Ser Gly Ala Pro Pro Pro Ser Xaa
        35                  40
```

```
<210> SEQ ID NO 61
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (16)..(16)
<223> OTHER INFORMATION: Glu in position 16 forms a lactam bridge with
      Lys in position 20
<220> FEATURE:
<221> NAME/KEY: MOD_RES
<222> LOCATION: (20)..(20)
<223> OTHER INFORMATION: Lys in position 20 forms a lactam bridge with
      Glu in position 16
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 61

Xaa Xaa Gln Gly Thr Phe Thr Ser Asp Tyr Ser Lys Gln Leu Asp Glu
1               5                   10                  15

Gln Arg Ala Lys Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 62
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7-Bis-carboxymethyl-[1,4,7]triazonan-
      1-yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 62

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40
```

-continued

```
<210> SEQ ID NO 63
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7-Bis-carboxymethyl-[1,4,7]triazonan-
      1-yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 63

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 64
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2-[2-(4,7-Bis-carboxymethyl-[1,4,7]triazonan-
      1-yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 64

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 65
<211> LENGTH: 40
<212> TYPE: PRT
<213> ORGANISM: Artificial Sequence
```

```
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (7)..(7)
<223> OTHER INFORMATION: Xaa is Aminoisobutyric acid (Aib)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2-[2-(4,7-Bis-carboxymethyl-[1,4,7]triazonan-
      1-yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 65

Xaa Ser Gln Gly Thr Phe Xaa Ser Asp Leu Ser Lys Gln Xaa Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 66
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 66

Xaa Xaa Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 67
<211> LENGTH: 40
<212> TYPE: PRT
<213> ORGANISM: Artificial Sequence
```

```
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with
      (4,7,10-Tris-carboxymethyl-1,4,7,10-tetraaza-cyclododec-1-yl)-
      acetyl
<220> FEATURE:
<221> NAME/KEY: MOD_RES
<222> LOCATION: (40)..(40)
<223> OTHER INFORMATION: Amidated C-terminus

<400> SEQUENCE: 67

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 68
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 68

Xaa Ser Gln Gly Thr Phe Thr Ser Asp Leu Ser Lys Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 69
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)
```

```
<220> FEATURE:
<221> NAME/KEY: MOD_RES
<222> LOCATION: (40)..(40)
<223> OTHER INFORMATION: Xaa is Cys derivatized with
      2-[2-(4,7-Bis-carboxymethyl-[1,4,7]triazonan-
      1-yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 69

Xaa Ser Gln Gly Thr Phe Thr Ser Asp Ile Ser Lys Gln Xaa Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 70
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with
      2-[2-(4,7-Bis-carboxymethyl-[1,4,7]triazonan-
      1-yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 70

Xaa Ser Gln Gly Thr Phe Thr Ser Asp Ile Ser Lys Gln Xaa Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 71
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)
```

```
<220> FEATURE:
<221> NAME/KEY: MOD_RES
<222> LOCATION: (40)..(40)
<223> OTHER INFORMATION: Xaa is Cys derivatized with
      1-{2-[2-(4,7-bis-carboxymethyl-[1,4,7]triazonan-
      1-yl)-acetylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 71

Xaa Ser Gln Gly Thr Phe Thr Ser Asp Ile Ser Lys Gln Xaa Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 72
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)
<220> FEATURE:
<221> NAME/KEY: MOD_RES
<222> LOCATION: (40)..(40)
<223> OTHER INFORMATION: Xaa is Cys derivatized with 1-{2-[(S)-4-(4,7-
      bis-carboxymethyl-[1,4,7]triazonan-
      1-yl)-4-carboxy-butyrylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 72

Xaa Ser Gln Gly Thr Phe Thr Ser Asp Ile Ser Lys Gln Xaa Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 73
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (14)..(14)
<223> OTHER INFORMATION: Xaa is L-Norleucine (Nle)
```

<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 73

Xaa Ser Gln Gly Thr Phe Thr Ser Asp Leu Ser Lys Gln Xaa Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 74
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (10)..(10)
<223> OTHER INFORMATION: Xaa is L-2-Fluorphenylalanine (2F-Phe)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 74

Xaa Ser Gln Gly Thr Phe Thr Ser Asp Xaa Ser Lys Gln Leu Glu Ser
1               5                   10                  15

Arg Arg Ala Gln Asp Phe Ile Glu Trp Leu Leu Ala Thr Gly Pro Glu
            20                  25                  30

Ser Gly Ala Pro Pro Pro Ser Xaa
        35                  40

<210> SEQ ID NO 75
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7-Bis-carboxymethyl-[1,4,7]triazonan-
      1-yl)-ethanesulfonyl]-ethyl

```
<220> FEATURE:
<221> NAME/KEY: MOD_RES
<222> LOCATION: (40)..(40)
<223> OTHER INFORMATION: Amidated C-terminus

<400> SEQUENCE: 75

Xaa Ser Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 76
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7-Bis-carboxymethyl-[1,4,7]triazonan-
      1-yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 76

Xaa Ser Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 77
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      1-{2-[2-(4,7-bis-carboxymethyl-[1,4,7]triazonan-
      1-yl)-acetylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus
```

```
<400> SEQUENCE: 77

Xaa Ser Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 78
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with 1-{2-[(S)-4-(4,7-
      bis-carboxymethyl-[1,4,7]triazonan-
      1-yl)-4-carboxy-butyrylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 78

Xaa Ser Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 79
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl

<400> SEQUENCE: 79

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 80
<211> LENGTH: 40
<212> TYPE: PRT
<213> ORGANISM: Artificial Sequence
```

```
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium

<400> SEQUENCE: 80

Xaa Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40

<210> SEQ ID NO 81
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Lys derivatized with
      (4,7,10-Tris-carboxymethyl-1,4,7,10-tetraaza-cyclododec-1-yl)-
      acetyl
<220> FEATURE:
<221> NAME/KEY: MOD_RES
<222> LOCATION: (40)..(40)
<223> OTHER INFORMATION: Amidated C-terminus

<400> SEQUENCE: 81

Xaa Ser Gln Gly Thr Phe Thr Ser Asp Tyr Ser Arg Gln Leu Glu Ser
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 82
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
```

```
<220> FEATURE:
<221> NAME/KEY: MOD_RES
<222> LOCATION: (40)..(40)
<223> OTHER INFORMATION: Amidated C-terminus

<400> SEQUENCE: 82

Xaa Xaa Gln Gly Thr Phe Thr Ser Asp Tyr Ser Lys Gln Leu Glu Ser
1               5                   10                  15

Ala Arg Ala Gln Asp Phe Ile Glu Trp Leu Leu Ala Thr Gly Pro Ser
            20                  25                  30

Ser Gly Ala Pro Pro Pro Ser Xaa
        35                  40

<210> SEQ ID NO 83
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus

<400> SEQUENCE: 83

Xaa Xaa Gln Gly Thr Phe Thr Ser Asp Tyr Ser Lys Gln Leu Glu Ser
1               5                   10                  15

Ala Arg Ala Gln Asp Phe Ile Glu Trp Leu Leu Ala Thr Gly Pro Ser
            20                  25                  30

Ser Gly Ala Pro Pro Pro Ser Xaa
        35                  40

<210> SEQ ID NO 84
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus
```

```
<400> SEQUENCE: 84

Xaa Ser Gln Gly Thr Phe Thr Ser Asp Tyr Ser Lys Gln Leu Glu Ser
1               5                   10                  15

Ala Arg Ala Gln Asp Phe Ile Glu Trp Leu Leu Ala Thr Gly Pro Ser
            20                  25                  30

Ser Gly Ala Pro Pro Pro Ser Xaa
        35                  40

<210> SEQ ID NO 85
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 85

Xaa Xaa Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 86
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl with complexed Gallium
<220> FEATURE:
<221> NAME/KEY: MOD_RES
<222> LOCATION: (40)..(40)
<223> OTHER INFORMATION: Amidated C-terminus
```

```
<400> SEQUENCE: 86

Xaa Xaa Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 87
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      1-{2-[2-(4,7-bis-carboxymethyl-[1,4,7]triazonan-
      1-yl)-acetylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus

<400> SEQUENCE: 87

Xaa Xaa Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 88
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with 1-{2-[(S)-4-(4,7-
      bis-carboxymethyl-[1,4,7]triazonan-
      1-yl)-4-carboxy-butyrylamino]ethyl}-2,5-dioxo-pyrrolidin-3-yl
<220> FEATURE:
<221> NAME/KEY: MOD_RES
<222> LOCATION: (40)..(40)
<223> OTHER INFORMATION: Amidated C-terminus
```

```
<400> SEQUENCE: 88

Xaa Xaa Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 89
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (2)..(2)
<223> OTHER INFORMATION: Xaa is D-Serine (s)
<220> FEATURE:
<221> NAME/KEY: MOD_RES
<222> LOCATION: (40)..(40)
<223> OTHER INFORMATION: Xaa is Cys derivatized with
      2-[2-(4,7-Bis-carboxymethyl-[1,4,7]triazonan-
      1-yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 89

Xaa Xaa Gln Gly Thr Phe Thr Ser Asp Tyr Ser Lys Gln Leu Asp Glu
1               5                   10                  15

Gln Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 90
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (1)..(1)
<223> OTHER INFORMATION: Xaa is L-4-Thiazolylalanine (Tza)
<220> FEATURE:
<221> NAME/KEY: MOD_RES
<222> LOCATION: (16)..(16)
<223> OTHER INFORMATION: Xaa is Aminoisobutyric acid (Aib)
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus
```

```
<400> SEQUENCE: 90

Xaa Ser His Gly Thr Phe Thr Ser Asp Tyr Ser Lys Gln Leu Asp Xaa
1               5                   10                  15

Arg Arg Ala Gln Glu Phe Ile Glu Trp Leu Leu Ala Thr Gly Pro Glu
            20                  25                  30

Ser Gly Ala Pro Pro Pro Ser Xaa
        35                  40

<210> SEQ ID NO 91
<211> LENGTH: 40
<212> TYPE: PRT
<213> ORGANISM: Artificial Sequence
<220> FEATURE:
<223> OTHER INFORMATION: artificial polypeptide
<220> FEATURE:
<221> NAME/KEY: MOD_RES
<222> LOCATION: (40)..(40)
<223> OTHER INFORMATION: Xaa is Cys derivatized with
      2-[2-(4,7,10-Tris-carboxymethyl-1,4,7,10-tetraaza-cyclododec-1-
      yl)-ethanesulfonyl]-ethyl
<220> FEATURE:
<221> NAME/KEY: MOD_RES
<222> LOCATION: (40)..(40)
<223> OTHER INFORMATION: Amidated C-terminus

<400> SEQUENCE: 91

His Ser Gln Gly Thr Phe Thr Ser Asp Tyr Ser Lys Gln Leu Glu Ser
1               5                   10                  15

Arg Arg Ala Gln Glu Phe Ile Glu Trp Leu Leu Ala Gly Gly Pro Glu
            20                  25                  30

Ser Gly Ala Pro Pro Pro Ser Xaa
        35                  40
```

SELECTIVE GLUCAGON RECEPTOR AGONISTS COMPRISING A CHELATING MOIETY FOR IMAGING PURPOSES

CROSS-REFERENCE TO RELATED APPLICATIONS

This application is a 35 U.S.C. § 371 filing of International Patent Application No. PCT/EP2016/080553, filed Dec. 12, 2016, which claims priority to European Patent Application No. 15307000.8, filed Dec. 14, 2015, the entire contents of which are hereby incorporated herein by reference.

FIELD OF THE INVENTION

The present invention relates to exendin-4 peptide analogues which selectively bind and activate the glucagon receptor and comprise a chelating moiety capable of binding a metal ion. Preferred metal ions are radionuclides, e.g. detectable by positron emission tomography (PET) or single photon emission computed tomography (SPECT). The obtained compounds are useful for visualizing cells overexpressing the glucagon receptor, in particular in the liver, as well as a method of detecting and treating neuroendocrine tumors characterized by an overexpression of the glucagon receptor. The invention includes a method of production of suitable agents.

BACKGROUND OF THE INVENTION

Exendin-4 is a 39 amino acid peptide which is produced by the salivary glands of the Gila monster (Heloderma suspectum) (Eng, J. et al., J. Biol. Chem., 267:7402-05, 1992). Exendin-4 is an activator of the glucagon-like peptide-1 (GLP-1) receptor, whereas it does not activate significantly the glucagon receptor.

The amino acid sequence of exendin-4 is shown as SEQ ID NO: 1

```
HGEGTFTSDLSKQMEEEAVRLFIEWLKNGGPSSGAPPPS-NH2
```

Glucagon is a 29-amino acid peptide which is released into the bloodstream when circulating glucose is low. Glucagon's amino acid sequence is shown as SEQ ID NO: 2.

```
HSQGTFTSDYSKYLDSRRAQDFVQWLMNT-OH
```

Positron emission tomography (PET) is a routinely used nuclear medicine imaging technique, capable of producing three dimensional images of subjects. After injection of a suitable radioactive tracer containing a positron-emitting radionuclide, a pair of orthogonal gamma rays is detected resulting from annihilation of a positron. Three dimensional images can be obtained after computational reconstruction; correct anatomical localization is frequently ensured by simultaneous recording of a CT X-ray scan.

Another nuclear medicine tomographic imaging technique to provide three dimensional images is single photon emission computed tomography (SPECT).

This method is based on detection of gamma rays emitted by a suitable radioisotope.

These methods are generally utilized to examine tissues and to monitor physiological processes e.g. by using 18-fluorodeoxy glucose for monitoring of metabolic activity. Alternatively, a marker radioisotope can be attached to a specific ligand to create a radio ligand displaying specificity to certain tissues or receptors, for example GPCR's.

Specific detection of a single receptor type by PET or SPECT requires a selective interaction of the tracer ligand with the receptor of interest. Selective GLP-1 receptor agonists with an imaging moiety have been described (Marti, B. et al. WO2006024275; Selvaraju, R. K. et al, Journal of Nuclear Medicine, 2013, 54, 1-6; Eriksson, O. et al, J Clin Endocrinol Metab, 2014, 99(5):1519-1524).

The present invention comprises imaging ligands that selectively interact with the glucagon receptor (GCG-R).

The peptides of this invention contain 4-Thiazolylalanine in position 1.

The use of 4-Thiazolylalanine in position 1 of a synthetic peptide has been described in WO07140284 for GLP-1 receptor agonists. Surprisingly and conversely, 4-Thiazolylalanine in the present invention provides highly active glucagon receptor agonists with strongly reduced activity at the GLP-1 receptor when compared to peptides that carry the natural histidine at position 1 (native glucagon).

The compounds of the present invention therefore are well suited for the investigation of the glucagon receptor in vivo using imaging technologies, such as PET or SPECT.

BRIEF SUMMARY OF THE INVENTION

Provided herein are exendin-4 analogs which potently and selectively bind and activate the glucagon receptor and comprise a chelating moiety capable of binding a metal ion, making the molecule suitable for imaging studies, for example PET studies. All the compounds carry the artificial amino acid 4-Thiazolylalanine at position 1. This surprisingly results in a higher selectivity towards the glucagon receptor versus the GLP1 receptor when identical compounds are compared to each other differing only at position 1 (Tza in position 1 instead of His). The present invention therefore provides highly selective glucagon receptor agonists which are well suited for the investigation of the glucagon receptor in vivo using an imaging technology, for example the PET technology.

The invention provides a peptidic compound having the formula (I).

```
                                                    (I)
Tza-X2-X3-Gly-Thr-Phe-X7-Ser-Asp-X10-Ser-X12-X13-

X14-X15-X16-X17-X18-Ala-X20-X21-Phe-Ile-Glu-Trp-

Leu-Leu-X28-X29-Gly-Pro-X32-Ser-Gly-Ala-Pro-Pro-

Pro-Ser-X40-R¹
```

X2 represents an amino acid selected from Ser and d-Ser,
X3 represents an amino acid selected from Gln and His,
X7 represents an amino acid selected from Thr and Aib,
X10 represents an amino acid residue selected from Tyr, Leu, Val, Ile, Phe, Phenylglycine, Thr, 2-Fluorophenylalanine, Cyclohexylglycine and tert-Leucine
X12 represents an amino acid selected from Lys, Arg and Cys(VS-DO3A),
X13 represents an amino acid selected from Gln, Tyr and Cys(VS-DO3A),
X14 represents an amino acid residue selected from Leu, Nle and Cys(VS-DO3A),
X15 represents an amino acid selected from Glu and Asp,
X16 represents an amino acid selected from Ser, Glu, Aib and Cys(VS-DO3A), X17 represents an amino acid selected from Arg, Gin, Lys, Ala and Cys(VS-DO3A), X18 represents an amino acid selected from Arg, Lys and Ala, X20 represents an amino acid selected from Gin, Glu, Aib, Lys and Cys(VS-DO3A), If X16 is Glu and X20 is Lys, the sidechains of X16 and X20 may form a cyclic ring via a lactam, X21 represents an amino acid residue selected from Asp and Glu, X28 represents an amino acid selected from Ala and β-Ala, X29 represents an amino acid residue selected from Gly and Thr, X32 represents an amino acid selected from Glu and Ser, X40 represents an amino acid selected from Cys(VS-DO3A), Cys(VS-NO2A), Cys(mal-DOTA), Cys(mal-NOTA), Cys(mal-NODAGA), Lys(DOTA), Lys(NOTA), Lys(PEG-DOTA) and Lys(VS-DO3A), X40 may be absent if one of the amino acids X12, X13, X14, X16, X17 or X20 is Cys(VS-DO3A), wherein DOTA, NOTA, DO3A, NO2A or NODAGA may be unloaded or loaded with a metal ion selected from $Gd^{3+}$, $Ga^{3+}$, $Cu^{2+}$, $(Al-F)^{2+}$, $Y^{3+}$, $Tc^{3+}$, $In^{3+}$, $Lu^{3+}$ and $Re^{3+}$, $R^1$ represents OH or $NH_2$;

or a metal complex or a salt or a solvate thereof.

A further embodiment of the invention provides a peptidic compound having the formula (I) wherein X2 represents an amino acid selected from Ser and d-Ser, X3 is Gln, X7 represents an amino acid selected from Thr and Aib, X10 represents an amino acid residue selected from Tyr, Leu, Ile, X12 is Lys, X13 is Gln, X14 represents an amino acid residue selected from Leu and Nle, X15 represents an amino acid selected from Glu and Asp, X16 represents an amino acid selected from Ser and Glu, X17 represents an amino acid selected from Arg and Gln, X18 is Arg, X20 represents an amino acid selected from Gln and Lys, If X16 is Glu and X20 is Lys, the sidechains of X16 and X20 may form a cyclic ring via a lactam, X21 represents an amino acid residue selected from Asp and Glu, X28 is Ala, X29 represents an amino acid residue selected from Gly and Thr, X32 is Glu, X40 is Cys(VS-DO3A), wherein DO3A, may be unloaded or loaded with a metal ion selected from $Gd^{3+}$, $Ga^{3+}$, $Cu^{2+}$, $(Al-F)^{2+}$, $Y^{3+}$, $Tc^{3+}$, $In^{3+}$, $Lu^{3+}$ and $Re^{3+}$, $R^1$ represents OH or $NH_2$;

or a metal complex or a salt or a solvate thereof.

Specific examples of a peptidic compound of formula (I) are the compounds of SEQ ID NO: 3 to 90 as well as salts or solvates thereof.

Specific examples of a peptidic compound of formula (I) are the compounds of SEQ ID NO: 6, 8, 13, 14, 35, 36, 49, 50, 60, 61, 79, 80, 85 and 86 as well as salts or solvates thereof.

A further embodiment of the invention provides a peptidic compound having the formula (I), wherein DOTA, NOTA, DO3A, NO2A or NODAGA is unloaded.

A further embodiment of the invention provides a peptidic compound having the formula (I) wherein DOTA, NOTA, DO3A, NO2A or NODAGA is loaded with a metal ion selected from $Gd^{3+}$, $Ga^{3+}$, $Cu^{2+}$, $(Al-F)^{2+}$, $Y^{3+}$, $Tc^{3+}$, $In^{3+}$, $Lu^{3+}$ and $Re^{3+}$.

A further embodiment of the invention provides a peptidic compound having the formula (I) wherein DOTA, NOTA, DO3A, NO2A or NODAGA is loaded with a metal ion $Ga^{3+}$.

A further embodiment of the invention provides a peptidic compound having the formula (I) wherein DOTA, NOTA, DO3A, NO2A or NODAGA is loaded with a metal ion $Gd^{3+}$.

A further embodiment of the invention provides a peptidic compound having the formula (I) wherein DOTA, NOTA, DO3A, NO2A or NODAGA is loaded with a metal radionucleotide ion $(Cu-64)^{2+}$, $(Ga-68)^{3+}$, $(Al-F-18)^{2+}$, $(Y-86)^{3+}$.

A further embodiment of the invention provides a peptidic compound having the formula (I) wherein DOTA, NOTA, DO3A, NO2A or NODAGA is loaded with one metal radionucleotide ion $(Ga-67)^{3+}$, $(Tc-99)^{3+}$, $(In-111)^{3+}$.

A further embodiment of the invention provides a peptidic compound having the formula (I) wherein DOTA, NOTA, DO3A, NO2A or NODAGA is loaded with one metal radionucleotide ion selected from $(Cu-67)^{2+}$, $(Y-90)^{3+}$, $(In-111)^{3+}$, $(Lu-177)^{3+}$, $(Re-186)^{3+}$ and $(Re-188)^{3+}$.

Preferred compounds are the peptides with SEQ ID No. 3 to 90 listed in table 1 or a metal complex or a salt or a solvate thereof.

TABLE 1

Sequences

| SEQ. ID | Sequence |
| --- | --- |
| 1 | H-G-E-G-T-F-T-S-D-L-S-K-Q-M-E-E-A-V-R-L-F-I-E-W-L-K-N-G-G-P-S-S-G-A-P-P-P-S-NH2 |
| 2 | H-S-Q-G-T-F-T-S-D-Y-S-K-Y-L-D-S-R-R-A-Q-D-F-V-Q-W-L-M-N-T-OH |
| 3 | Tza-S-Q-G-T-F-T-S-D-Y-S-K-Q-L-E-S-R-R-A-Q-E-F-I-E-W-L-L-A-G-G-P-E-S-G-A-P-P-P-S-C(mal-DOTA)-NH2 |
| 4 | Tza-S-Q-G-T-F-T-S-D-Y-S-K-Q-L-E-S-R-R-A-Q-E-F-I-E-W-L-L-A-G-G-P-E-S-G-A-P-P-P-S-C(mal-NOTA)-NH2 |

TABLE 1-continued

Sequences

| SEQ. ID | Sequence |
|---|---|
| 5 | Tza-S-Q-G-T-F-T-S-D-Y-S-K-Q-L-E-S-R-R-A-Q-E-F-I-E-W-L-L-A-G-G-P-E-S-G-A-P-P-P-S-C(mal-NODAGA)-NH2 |
| 6 | Tza-S-Q-G-T-F-T-S-D-Y-S-K-Q-L-E-S-R-R-A-Q-E-F-I-E-W-L-L-A-G-G-P-E-S-G-A-P-P-P-S-C(VS-DO3A)-NH2 |
| 7 | Tza-S-Q-G-T-F-T-S-D-Y-S-K-Q-L-E-S-R-R-A-Q-E-F-I-E-W-L-L-A-G-G-P-E-S-G-A-P-P-P-S-C(mal-DOTA(Ga))-NH2 |
| 8 | Tza-S-Q-G-T-F-T-S-D-Y-S-K-Q-L-E-S-R-R-A-Q-E-F-I-E-W-L-L-A-G-G-P-E-S-G-A-P-P-P-S-C(VS-DO3A(Ga))-NH2 |
| 9 | Tza-S-Q-G-T-F-T-S-D-Y-S-K-Q-L-E-S-R-R-A-Q-E-F-I-E-W-L-L-A-G-G-P-E-S-G-A-P-P-P-S-C(mal-NOTA(Ga))-NH2 |
| 10 | Tza-S-Q-G-T-F-T-S-D-Y-S-K-Q-L-E-S-R-R-A-Q-E-F-I-E-W-L-L-A-G-G-P-E-S-G-A-P-P-P-S-C(mal-NODAGA(Ga))-NH2 |
| 11 | Tza-S-Q-G-T-F-T-S-D-Tle-S-K-Q-Nle-E-S-R-R-A-Q-E-F-I-E-W-L-L-Bal-G-G-P-E-S-G-A-P-P-P-S-C(VS-DO3A)-NH2 |
| 12 | Tza-S-Q-G-T-F-T-S-D-Tle-S-K-Q-Nle-E-S-R-R-A-Q-E-F-I-E-W-L-L-Bal-G-G-P-E-S-G-A-P-P-P-S-C(VS-DO3A(Ga))-NH2 |
| 13 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(VS-DO3A)-NH2 |
| 14 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(VS-DO3A(Ga))-NH2 |
| 15 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(mal-DOTA)-NH2 |
| 16 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(mal-NOTA)-NH2 |
| 17 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(mal-NODAGA)-NH2 |
| 18 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(mal-DOTA(Ga))-NH2 |
| 19 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(mal-NOTA(Ga))-NH2 |
| 20 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(mal-NODAGA(Ga))-NH2 |
| 21 | Tza-s-Q-G-T-F-T-S-D-Y-S-K-Q-L-E-S-R-R-A-Q-E-F-I-E-W-L-L-A-G-G-P-E-S-G-A-P-P-P-S-C(VS-DO3A(Ga))-NH2 |
| 22 | Tza-s-Q-G-T-F-T-S-D-Y-S-K-Q-L-D-S-R-A-A-Q-D-F-I-E-W-L-L-A-G-G-P-S-S-G-A-P-P-P-S-C(VS-DO3A)-NH2 |
| 23 | Tza-s-Q-G-T-F-T-S-D-Y-S-K-Q-L-D-S-R-A-A-Q-D-F-I-E-W-L-L-A-G-G-P-S-S-G-A-P-P-P-S-C(VS-DO3A(Ga))-NH2 |
| 24 | Tza-s-Q-G-T-F-T-S-D-Y-S-K-Q-L-E-S-Q-R-A-Q-D-F-I-E-W-L-L-A-G-G-P-S-S-G-A-P-P-P-S-C(VS-DO3A(Ga))-NH2 |
| 25 | Tza-s-Q-G-T-F-T-S-D-Y-S-K-Q-L-E-S-Q-R-A-Q-D-F-I-E-W-L-L-A-G-G-P-S-S-G-A-P-P-P-S-C(VS-DO3A)-NH2 |
| 26 | Tza-S-Q-G-T-F-T-S-D-Y-S-R-Q-L-E-S-R-R-A-Q-E-F-I-E-W-L-L-A-G-G-P-E-S-G-A-P-P-P-S-K(DOTA)-NH2 |
| 27 | Tza-S-Q-G-T-F-T-S-D-Y-S-R-Q-L-E-S-R-R-A-Q-E-F-I-E-W-L-L-A-G-G-P-E-S-G-A-P-P-P-S-K(DOTA(Ga))-NH2 |
| 28 | Tza-S-Q-G-T-F-T-S-D-Y-S-R-Q-L-E-S-R-R-A-Q-E-F-I-E-W-L-L-A-G-G-P-E-S-G-A-P-P-P-S-K(NOTA)-NH2 |
| 29 | Tza-S-Q-G-T-F-T-S-D-Y-S-R-Q-L-E-S-R-R-A-Q-E-F-I-E-W-L-L-A-G-G-P-E-S-G-A-P-P-P-S-K(PEG-NOTA)-NH2 |

TABLE 1-continued

Sequences

| SEQ. ID | Sequence |
|---|---|
| 30 | Tza-S-Q-G-T-F-T-S-D-Y-S-R-Q-L-E-S-R-R-A-Q-E-F-I-E-W-L-L-A-G-G-P-E-S-G-A-P-P-P-S-K(PEG-NOTA(Ga))-NH2 |
| 31 | Tza-S-Q-G-T-F-Aib-S-D-L-A-K-Q-Nle-E-S-R-R-A-Q-D-F-I-E-W-L-L-A-T-G-P-E-S-G-A-P-P-P-S-C(VS-DO3A)-NH2 |
| 32 | Tza-S-Q-G-T-F-Aib-S-D-L-A-K-Q-Nle-E-S-R-R-A-Q-D-F-I-E-W-L-L-A-T-G-P-E-S-G-A-P-P-P-S-C(VS-DO3A(Ga))-NH2 |
| 33 | Tza-S-Q-G-T-F-T-S-D-Y-S-K-Q-L-E-S-R-R-A-Q-E-F-I-E-W-L-L-A-T-G-P-E-S-G-A-P-P-P-S-C(VS-DO3A)-NH2 |
| 34 | Tza-S-Q-G-T-F-T-S-D-Y-S-K-Q-L-E-S-R-R-A-Q-E-F-I-E-W-L-L-A-T-G-P-E-S-G-A-P-P-P-S-C(VS-DO3A(Ga))-NH2 |
| 35 | Tza-S-Q-G-T-F-T-S-D-I-S-K-Q-Nle-E-S-R-R-A-Q-E-F-I-E-W-L-L-A-T-G-P-E-S-G-A-P-P-P-S-C(VS-DO3A)-NH2 |
| 36 | Tza-S-Q-G-T-F-T-S-D-I-S-K-Q-Nle-E-S-R-R-A-Q-E-F-I-E-W-L-L-A-T-G-P-E-S-G-A-P-P-P-S-C(VS-DO3A(Ga))-NH2 |
| 37 | Tza-S-Q-G-T-F-T-S-D-Y-S-C(VS-DO3A)-Q-L-E-S-R-R-A-Q-E-F-I-E-W-L-L-A-G-G-P-E-S-G-A-P-P-P-S-NH2 |
| 38 | Tza-S-Q-G-T-F-T-S-D-Y-S-K-C(VS-DO3A)-L-E-S-R-R-A-Q-E-F-I-E-W-L-L-A-G-G-P-E-S-G-A-P-P-P-S-NH2 |
| 39 | Tza-S-Q-G-T-F-T-S-D-Y-S-K-Q-C(VS-DO3A)-E-S-R-R-A-Q-E-F-I-E-W-L-L-A-G-G-P-E-S-G-A-P-P-P-S-NH2 |
| 40 | Tza-S-Q-G-T-F-T-S-D-Y-S-K-Q-L-E-C(VS-DO3A)-R-R-A-Q-E-F-I-E-W-L-L-A-G-G-P-E-S-G-A-P-P-P-S-NH2 |
| 41 | Tza-S-Q-G-T-F-T-S-D-Y-S-K-Q-L-E-S-C(VS-DO3A)-R-A-Q-E-F-I-E-W-L-L-A-G-G-P-E-S-G-A-P-P-P-S-NH2 |
| 42 | Tza-S-Q-G-T-F-T-S-D-Y-S-K-Q-L-E-S-R-R-A-C(VS-DO3A)-E-F-I-E-W-L-L-A-G-G-P-E-S-G-A-P-P-P-S-NH2 |
| 43 | Tza-S-Q-G-T-F-T-S-D-Y-S-R-Q-L-E-S-R-R-A-Q-E-F-I-E-W-L-L-A-T-G-P-E-S-G-A-P-P-P-S-K(VS-DO3A)-NH2 |
| 44 | Tza-S-Q-G-T-F-T-S-D-Y-S-R-Q-L-E-S-R-R-A-Q-E-F-I-E-W-L-L-A-T-G-P-E-S-G-A-P-P-P-S-K(VS-DO3A(Ga))-NH2 |
| 45 | Tza-S-Q-G-T-F-T-S-D-Y-S-R-Q-L-E-S-R-R-A-Q-E-F-I-E-W-L-L-A-T-G-P-E-S-G-A-P-P-P-S-K(DOTA)-NH2 |
| 46 | Tza-S-Q-G-T-F-T-S-D-Y-S-R-Q-L-E-S-R-R-A-Q-E-F-I-E-W-L-L-A-T-G-P-E-S-G-A-P-P-P-S-K(DOTA(Ga))-NH2 |
| 47 | Tza-S-Q-G-T-F-T-S-D-T-S-K-Q-L-E-S-R-R-A-Q-E-F-I-E-W-L-L-A-T-G-P-E-S-G-A-P-P-P-S-C(VS-DO3A)-NH2 |
| 48 | Tza-S-Q-G-T-F-T-S-D-T-S-K-Q-L-E-S-R-R-A-Q-E-F-I-E-W-L-L-A-T-G-P-E-S-G-A-P-P-P-S-C(VS-DO3A(Ga))-NH2 |
| 49 | Tza-S-Q-G-T-F-T-S-D-Y-S-K-Q-L-D-E-Q-R-A-Q-E-F-I-E-W-L-L-A-T-G-P-E-S-G-A-P-P-P-S-C(VS-DO3A)-NH2 |
| 50 | Tza-S-Q-G-T-F-T-S-D-Y-S-K-Q-L-D-E-Q-R-A-Q-E-F-I-E-W-L-L-A-T-G-P-E-S-G-A-P-P-P-S-C(VS-DO3A(Ga))-NH2 |
| 51 | Tza-S-Q-G-T-F-Aib-S-D-L-S-K-Q-Nle-E-S-R-R-A-K-D-F-I-E-W-L-L-A-T-G-P-E-S-G-A-P-P-P-S-C(VS-DO3A)-NH2 |
| 52 | Tza-S-Q-G-T-F-Aib-S-D-L-S-K-Q-Nle-E-S-R-R-A-K-D-F-I-E-W-L-L-A-T-G-P-E-S-G-A-P-P-P-S-C(VS-DO3A(Ga))-NH2 |
| 53 | Tza-S-Q-G-T-F-T-S-D-Y-S-R-Q-L-E-S-R-R-A-Q-E-F-I-E-W-L-L-A-T-G-P-E-S-G-A-P-P-P-S-K(NOTA)-NH2 |
| 54 | Tza-S-Q-G-T-F-T-S-D-Y-S-K-Q-L-E-Aib-R-R-A-Q-E-F-I-E-W-L-L-A-G-G-P-E-S-G-A-P-P-P-S-C(VS-DO3A)-NH2 |

TABLE 1-continued

Sequences

| SEQ. ID | Sequence |
|---|---|
| 55 | Tza-S-Q-G-T-F-T-S-D-Y-S-K-Q-L-E-Aib-R-R-A-Q-E-F-I-E-W-L-L-A-G-G-P-E-S-G-A-P-P-P-S-C(VS-DO3A(Ga))-NH2 |
| 56 | Tza-S-H-G-T-F-T-S-D-Y-S-K-Q-L-E-Aib-R-R-A-Q-E-F-I-E-W-L-L-A-T-G-P-E-S-G-A-P-P-P-S-C(VS-DO3A)-NH2 |
| 57 | Tza-S-H-G-T-F-T-S-D-Y-S-K-Q-L-E-Aib-K-K-A-Q-E-F-I-E-W-L-L-A-T-G-P-E-S-G-A-P-P-P-S-C(VS-DO3A)-NH2 |
| 58 | Tza-s-Q-G-T-F-T-S-D-Y-S-K-Q-L-D-Aib-K-K-A-Q-E-F-I-E-W-L-L-A-T-G-P-E-S-G-A-P-P-P-S-C(VS-DO3A)-NH2 |
| 59 | Tza-S-H-G-T-F-T-S-D-I-S-K-Q-L-D-E-Q-R-A-Q-E-F-I-E-W-L-L-A-T-G-P-E-S-G-A-P-P-P-S-C(VS-DO3A)-NH2 |
| 60 | L-A-T-G-P-E-S-G-A-P-P-P-S-C(VS-DO3A)-NH2 |
| 61 | L-A-T-G-P-E-S-G-A-P-P-P-S-C(VS-DO3A(Ga))-NH2 |
| 62 | Tza-S-Q-G-T-F-T-S-D-Y-S-K-Q-L-E-S-R-R-A-Q-E-F-I-E-W-L-L-A-G-G-P-E-S-G-A-P-P-P-S-C(VS-NO2A)-NH2 |
| 63 | Tza-S-Q-G-T-F-T-S-D-Y-S-K-Q-L-E-S-R-R-A-Q-E-F-I-E-W-L-L-A-G-G-P-E-S-G-A-P-P-P-S-C(VS-NO2A(Ga))-NH2 |
| 64 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(VS-NO2A)-NH2 |
| 65 | Tza-S-Q-G-T-F-Aib-S-D-L-S-K-Q-Nle-E-S-R-R-A-Q-D-F-I-E-W-L-L-A-T-G-P-E-S-G-A-P-P-P-S-C(VS-NO2A(Ga))-NH2 |
| 66 | Tza-s-Q-G-T-F-T-S-D-Y-S-K-Q-L-E-S-R-R-A-Q-E-F-I-E-W-L-L-A-G-G-P-E-S-G-A-P-P-P-S-C(VS-DO3A)-NH2 |
| 67 | Tza-S-Q-G-T-F-T-S-D-Y-S-K-Q-L-E-S-R-R-A-Q-E-F-I-E-W-L-L-A-G-G-P-E-S-G-A-P-P-P-S-K(DOTA)-NH2 |
| 68 | Tza-S-Q-G-T-F-T-S-D-L-S-K-Q-L-E-S-R-R-A-Q-E-F-I-E-W-L-L-A-T-G-P-E-S-G-A-P-P-P-S-C(VS-DO3A)-NH2 |
| 69 | Tza-S-Q-G-T-F-T-S-D-I-S-K-Q-Nle-E-S-R-R-A-Q-E-F-I-E-W-L-L-A-T-G-P-E-S-G-A-P-P-P-S-C(VS-NO2A)-NH2 |
| 70 | Tza-S-Q-G-T-F-T-S-D-I-S-K-Q-Nle-E-S-R-R-A-Q-E-F-I-E-W-L-L-A-T-G-P-E-S-G-A-P-P-P-S-C(VS-NO2A(Ga))-NH2 |
| 71 | Tza-S-Q-G-T-F-T-S-D-I-S-K-Q-Nle-E-S-R-R-A-Q-E-F-I-E-W-L-L-A-T-G-P-E-S-G-A-P-P-P-S-C(mal-NOTA)-NH2 |
| 72 | Tza-S-Q-G-T-F-T-S-D-I-S-K-Q-Nle-E-S-R-R-A-Q-E-F-I-E-W-L-L-A-T-G-P-E-S-G-A-P-P-P-S-C(mal-NODAGA)-NH2 |
| 73 | Tza-S-Q-G-T-F-T-S-D-L-S-K-Q-Nle-E-S-R-R-A-Q-E-F-I-E-W-L-L-A-T-G-P-E-S-G-A-P-P-P-S-C(VS-DO3A)-NH2 |
| 74 | Tza-S-Q-G-T-F-T-S-D-$_2$F-Phe-S-K-Q-L-E-S-R-R-A-Q-D-F-I-E-W-L-L-A-T-G-P-E-S-G-A-P-P-P-S-C(VS-DO3A)-NH2 |
| 75 | Tza-S-Q-G-T-F-T-S-D-Y-S-K-Q-L-D-E-Q-R-A-Q-E-F-I-E-W-L-L-A-T-G-P-E-S-G-A-P-P-P-S-C(VS-NO2A)-NH2 |
| 76 | Tza-S-Q-G-T-F-T-S-D-Y-S-K-Q-L-D-E-Q-R-A-Q-E-F-I-E-W-L-L-A-T-G-P-E-S-G-A-P-P-P-S-C(VS-NO2A(Ga))-NH2 |
| 77 | Tza-S-Q-G-T-F-T-S-D-Y-S-K-Q-L-D-E-Q-R-A-Q-E-F-I-E-W-L-L-A-T-G-P-E-S-G-A-P-P-P-S-C(mal-NOTA)-NH2 |
| 78 | Tza-S-Q-G-T-F-T-S-D-Y-S-K-Q-L-D-E-Q-R-A-Q-E-F-I-E-W-L-L-A-T-G-P-E-S-G-A-P-P-P-S-C(mal-NODAGA)-NH2 |
| 79 | Tza-S-Q-G-T-F-T-S-D-Y-S-K-Q-L-E-S-R-R-A-Q-E-F-I-E-W-L-L-A-G-G-P-E-S-G-A-P-P-P-S-C(VS-DO3A)-OH |
| 80 | Tza-S-Q-G-T-F-T-S-D-Y-S-K-Q-L-E-S-R-R-A-Q-E-F-I-E-W-L-L-A-G-G-P-E-S-G-A-P-P-P-S-C(VS-DO3A(Ga))-OH |

TABLE 1-continued

Sequences

| SEQ. ID | Sequence |
|---|---|
| 81 | Tza-S-Q-G-T-F-T-S-D-Y-S-R-Q-L-E-S-R-R-A-Q-E-F-I-E-W-L-L-A-T-G-P-E-S-G-A-P-P-P-S-K(DOTA)-NH2 |
| 82 | Tza-s-Q-G-T-F-T-S-D-Y-S-K-Q-L-E-S-A-R-A-Q-D-F-I-E-W-L-L-A-T-G-P-S-S-G-A-P-P-P-S-C(VS-DO3A)-NH2 |
| 83 | Tza-s-Q-G-T-F-T-S-D-Y-S-K-Q-L-E-S-A-R-A-Q-D-F-I-E-W-L-L-A-T-G-P-S-S-G-A-P-P-P-S-C(VS-DO3A(Ga))-NH2 |
| 84 | Tza-S-Q-G-T-F-T-S-D-Y-S-K-Q-L-E-S-A-R-A-Q-D-F-I-E-W-L-L-A-T-G-P-S-S-G-A-P-P-P-S-C(VS-DO3A)-NH2 |
| 85 | Tza-s-Q-G-T-F-T-S-D-Y-S-K-Q-L-D-E-Q-R-A-Q-E-F-I-E-W-L-L-A-T-G-P-E-S-G-A-P-P-P-S-C(VS-DO3A)-NH2 |
| 86 | Tza-s-Q-G-T-F-T-S-D-Y-S-K-Q-L-D-E-Q-R-A-Q-E-F-I-E-W-L-L-A-T-G-P-E-S-G-A-P-P-P-S-C(VS-DO3A(Ga))-NH2 |
| 87 | Tza-s-Q-G-T-F-T-S-D-Y-S-K-Q-L-D-E-Q-R-A-Q-E-F-I-E-W-L-L-A-T-G-P-E-S-G-A-P-P-P-S-C(mal-NOTA)-NH2 |
| 88 | Tza-s-Q-G-T-F-T-S-D-Y-S-K-Q-L-D-E-Q-R-A-Q-E-F-I-E-W-L-L-A-T-G-P-E-S-G-A-P-P-P-S-C(mal-NODAGA)-NH2 |
| 89 | Tza-s-Q-G-T-F-T-S-D-Y-S-K-Q-L-D-E-Q-R-A-Q-E-F-I-E-W-L-L-A-T-G-P-E-S-G-A-P-P-P-S-C(VS-NO$_2$A)-NH2 |
| 90 | Tza-S-H-G-T-F-T-S-D-Y-S-K-Q-L-D-Aib-R-R-A-Q-E-F-I-E-W-L-L-A-T-G-P-E-S-G-A-P-P-P-S-C(VS-DO3A)-NH2 |
| 91 | H-S-Q-G-T-F-T-S-D-Y-S-K-Q-L-E-S-R-R-A-Q-E-F-I-E-W-L-L-A-G-G-P-E-S-G-A-P-P-P-S-C(VS-DO3A)-NH2 |

In sequence 60 and 61, asterisk ("*") indicates the formation of a lactam bridge between Glu16 and Lys20.

The compounds of the invention are capable of specifically binding to the glucagon receptor. The compounds of the invention are glucagon receptor agonists as determined by the observation that they are capable of stimulating intracellular cAMP formation upon binding at the receptor for glucagon. The compounds exhibit at least a relative activity of 0.1%, preferably 0.5%, more preferably 1.0% and even more preferably 10.0% compared to that of natural glucagon at the glucagon receptor.

The compounds of the invention also activate the GLP1 receptor as determined by the observation that they are capable of stimulating intracellular cAMP formation upon binding at the receptor for GLP1. The activity of a given compound of this invention (expressed by its activity relative to the activity of GLP1 at the GLP1 receptor) is below 1%, more preferably below 0.5% and even more preferably below 0.1% compared to the activity of the same compound at the glucagon receptor (expressed by its activity relative to the activity of glucagon at the glucagon receptor).

Surprisingly, it was found that peptidic compounds of the formula I with 4-Thiazolylalanine at position 1 showed increased glucagon receptor activation and strongly increased selectivity towards the activity on the GLP-1 receptor compared to derivatives having a histidine at this position. Histidine is the naturally occurring amino acid in glucagon at position 1 and has been shown to be important for the activation mechanism of the glucagon receptor (Unson, C. G. et al, Arch. Biochem. Biophys., 300, 747-750, 1993).

Further, the compounds of the invention preferably have a favourable stability at acidic or physiological pH values, e.g., at pH 4.5 or at pH 7.4 at 4° C., 25° C. or 40° C. Preferably, the purity of the compounds in these buffers after 7 days at 25° C. is greater than 80% and after 14 days greater than 60%.

Furthermore, the compounds of the invention contain a chelating moiety capable of binding a metal ion, making the molecule suitable for imaging studies, for example PET or SPECT studies. The chelating moiety represents a non-cyclic or cyclic structure containing electron pair donating elements to ensure strong binding to the metal cation. Strong chelation is a prerequisite for use as an imaging modality in order to prevent leaching of the radioisotope, which may result in systemic toxicity, increased background signal and reduction of the signal at the area of interest. Choice of an optimal chelating moiety depends on the nature of the complexed radiometal. Exemplifying frequently used chelating moieties and their corresponding names are listed in Scheme 1, more examples can e.g. be found in Wadas T. J. et al, Chem. Rev. 2010, 110, 2858-2902.

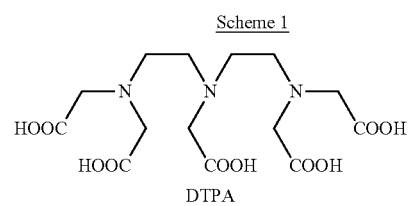

Scheme 1

DTPA

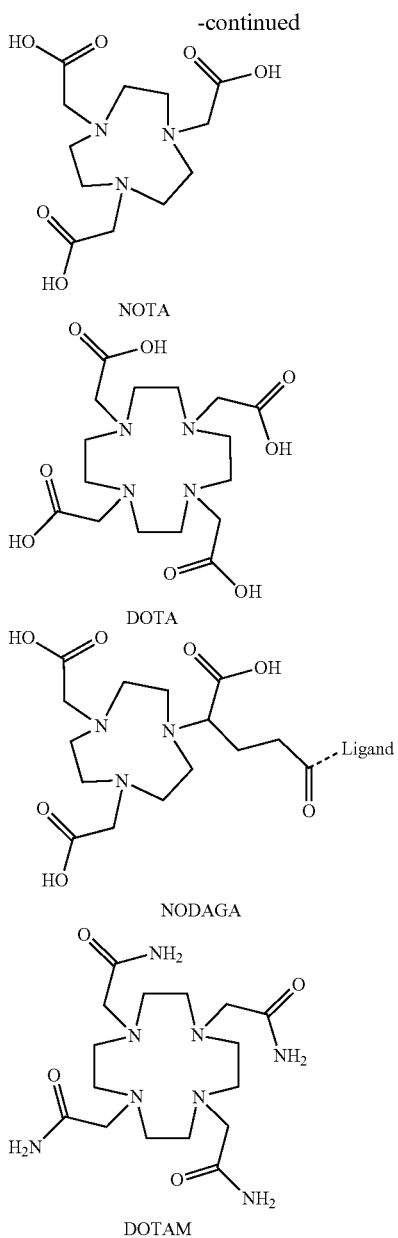

DETAILED DESCRIPTION OF THE INVENTION

Definitions

The amino acid sequences of the present invention contain the conventional one letter and three letter codes for naturally occurring amino acids, as well as generally accepted three letter codes for other amino acids, such as Nle (Norleucine).

Furthermore, the following codes were used for the amino acids shown in Table 2.

TABLE 2

| Unnatural amino acids | | |
|---|---|---|
| Structure | Name | Code |
|  | L-4-Thiazolylalanine | Tza |
|  | Aminoisobutyric acid | Aib |
|  | beta-Alanine | Bal |
|  | L-tert-Leucine | Tle |
|  | L-2-Fluorphenylalanine | 2F-Phe |
|  | D-Serine | s |
|  | L-norleucine | Nle |

In certain embodiments, i.e. when the compound of formula (I) comprises genetically encoded amino acid residues, the invention further provides a nucleic acid (which may be DNA or RNA) encoding said compound, an expression vector comprising such a nucleic acid, and a host cell containing such a nucleic acid or expression vector.

In a further aspect, the present invention provides a composition comprising a compound of the invention in admixture with a carrier. In preferred embodiments, the composition is a pharmaceutically acceptable composition and the carrier is a pharmaceutically acceptable carrier. The compound of the invention may be in the form of a metal complex, e.g. a gallium(III) complex, a salt, e.g. a pharmaceutically acceptable salt, or a solvate, e.g. a hydrate. In still a further aspect, the present invention provides a composition for use in a method of medical treatment including diagnostic treatment, particularly in human medicine.

Compounds of this invention and formulation thereof may primarily be used to visualize the glucagon receptor in living subjects and relevant tissues, preferably using the PET technology.

The term "native exendin-4" refers to native exendin-4 having the sequence (SEQ ID NO: 1)
HGEGTFTSDLSKQMEEEAVRLFIEWLKNGGPSSGAPPPS-NH$_2$.

The invention provides peptidic compounds as defined above.

The peptidic compounds of the present invention comprise a linear backbone of amino carboxylic acids linked by peptide, i.e. carboxamide bonds. Preferably, the amino carboxylic acids are α-amino carboxylic acids and more preferably L-α-amino carboxylic acids, unless indicated otherwise. The peptidic compounds comprise a backbone sequence of 39 or 40 amino carboxylic acids.

For the avoidance of doubt, in the definitions provided herein, it is generally intended that the sequence of the peptidic moiety differs from native exendin-4 at least at one of those positions which are stated to allow variation. Amino acids within the peptide moiety can be considered to be numbered consecutively from 1 to 40 in the conventional N-terminal to C-terminal direction. Reference to a "position" within peptidic moiety should be constructed accordingly, as should reference to positions within native exendin-4 and other molecules, e.g., in exendin-4, His is at position 1, Gly at position 2, . . . , Met at position 14, . . . and Ser at position 39.

In a further aspect, the present invention provides a composition comprising a compound of the invention as described herein, a metal complex, or a salt or solvate thereof, in admixture with a carrier.

The invention also provides a composition wherein the composition is a pharmaceutically acceptable composition, and the carrier is a pharmaceutically acceptable carrier.

Peptide Synthesis

The skilled person is aware of a variety of different methods to prepare peptides that are described in this invention. These methods include but are not limited to synthetic approaches and recombinant gene expression. Thus, one way of preparing these peptides is the synthesis in solution or on a solid support and subsequent isolation and purification. A different way of preparing the peptides is gene expression in a host cell in which a DNA sequence encoding the peptide has been introduced. Alternatively, the gene expression can be achieved without utilizing a cell system. The methods described above may also be combined in any way.

A preferred way to prepare the peptides of the present invention is solid phase synthesis on a suitable resin. Solid phase peptide synthesis is a well established methodology (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989). Solid phase synthesis is initiated by attaching an N-terminally protected amino acid with its carboxy terminus to an inert solid support carrying a cleavable linker. This solid support can be any polymer that allows coupling of the initial amino acid, e.g. a trityl resin, a chlorotrityl resin, a Wang resin or a Rink amide resin in which the linkage of the carboxy group (or carboxamide for Rink resin) to the resin is sensitive to acid (when Fmoc strategy is used). The polymer support must be stable under the conditions used to deprotect the α-amino group during the peptide synthesis.

After the first amino acid has been coupled to the solid support, the α-amino protecting group of this amino acid is removed. The remaining protected amino acids are then coupled one after the other in the order represented by the peptide sequence using appropriate amide coupling reagents, for example BOP, HBTU, HATU or DIC (N,N'-diisopropylcarbodiimide)/HOBt (1-hydroxybenzotriazol), wherein BOP, HBTU and HATU are used with tertiary amine bases. Alternatively, the liberated N-terminus can be functionalized with groups other than amino acids, for example carboxylic acids, etc.

Finally the peptide is cleaved from the resin and deprotected. This can be achieved by using King's cocktail (D. S. King, C. G. Fields, G. B. Fields, Int. J. Peptide Protein Res. 36, 1990, 255-266). The raw material can then be purified by chromatography, e.g. preparative RP-HPLC, if necessary.

The synthesized peptide is then further modified by attaching a side chain which contains a chelating moiety capable of integration a metal ion, for example Ga$^{3+}$. In those cases where the attachment point in the peptide backbone is a lysine the side chain can be linked by the reaction with a suitable amidation group, e.g. a hydroxyl succinimide ester, or with a vinylsulfone group via Michael addition. In other cases, when the attachment side is a thiol of a cysteine, the side chain can be connected by the reaction with a maleimide functionality or with a vinylsulfone group via Michael addition. The raw material can then be deprotected as necessary and purified by chromatography, e.g. preparative RP-HPLC. The side chains attached to the compounds of this invention are summarized in table 3.

For the compounds of the present invention the building blocks listed in table 4 were used. With the exception of the building blocks VS-DO3A and VS-NO2A these building blocks were commercially available. The synthesis of VS-DO3A is described in Example 1, the synthesis of VS-NO2A can be performed in an analogous way.

TABLE 3

Side chains

| Side chain | Side chain structure | Side chain name |
| --- | --- | --- |
| mal-DOTA | 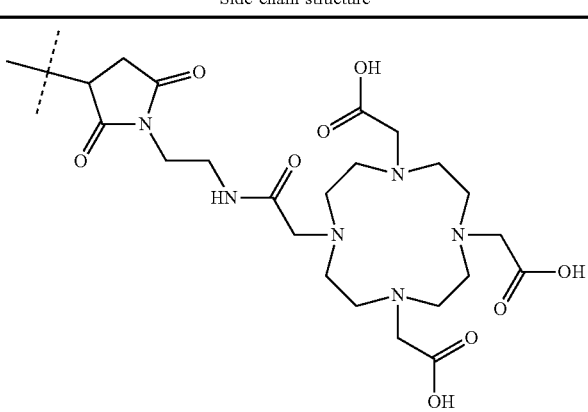 | 2,5-dioxo-1-{2-[2-(4,7,10-tris-carboxymethyl-1,4,7,10tetraaza-cyclododec-1-yl)-acetylamino]-ethyl}-pyrrolidin-3-yl |

TABLE 3-continued

| Side chain | Side chain structure | Side chain name |
|---|---|---|
| mal-NOTA | | 1-{2-[2-(4,7-bis-carboxymethyl-[1,4,7]triazonan-1-yl)-acetylamino]-ethyl}-2,5-dioxo-pyrrolidin-3-yl |
| mal-NODAGA | | 1-{2-[(S)-4-(4,7-bis-carboxymethyl-[1,4,7]triazonan-1-yl)-4-carboxy-butyrylamino]-ethyl}-2,5-dioxo-pyrrolidin-3-yl |
| DOTA | | (4,7,10-Tris-carboxymethyl-1,4,7,10-tetraaza-cyclododec-1-yl)-acetyl |
| NOTA | | (4,7-Bis-carboxymethyl-[1,4,7]triazonan-1-yl)-acetyl |
| PEG-NOTA | | 3-{2-[2-(2-{2-[3-(1-{2-[2-(4,7-Bis-carboxymethyl-[1,4,7]triazonan-1-yl)-acetylamino]-ethyl}-2,5-dioxo-pyrrolidin-3-ylsulfanyl)-propionylamino]-ethoxy}-ethoxy)-ethoxy]-ethoxy}-propionyl |

TABLE 3-continued

Side chains

| Side chain | Side chain structure | Side chain name |
| --- | --- | --- |
| VS-NO2A | | 2-[2-(4,7-bis-carboxymethyl-[1,4,7]triazonan-1-yl)-ethanesulfonyl]-ethyl |
| VS-DO3A | | 2-[2-(4,7,10-tris-carboxymethyl-1,4,7,10tetraaza-cyclododec-1-yl)-ethanesulfonyl]-ethyl |

TABLE 4

Relevant side chain building blocks

| Side chain building block | Building block structure |
| --- | --- |
| mal-DOTA building block | |
| mal-NOTA building block | |

TABLE 4-continued

Relevant side chain building blocks

| Side chain building block | Building block structure |
|---|---|
| mal-NODAGA building block | |
| DOTA building block | |
| NOTA building block | |
| SPDP-dPEG8-NHS ester | |
| VS-NO2A building block | |

TABLE 4-continued

Relevant side chain building blocks

| Side chain building block | Building block structure |
|---|---|
| VS-DO3A building block | 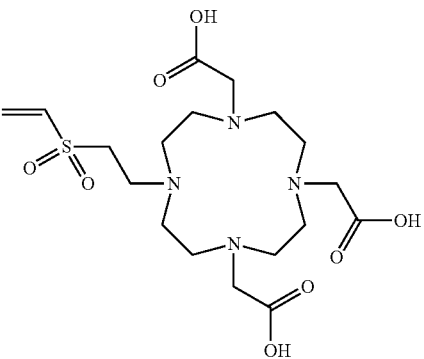 [SMILES: C=CS(=O)(=O)CCN1CCN(CC(=O)O)CCN(CC(=O)O)CCN(CC(=O)O)CC1] |

The complexing moiety at the side chain of the peptide can further be charged with a suitable metal ion, e.g. $Ga^{3+}$. To achieve this, the peptide with the side chain is heated with a suitable salt of the desired cation in a suitable solvent. The raw material can then be purified by chromatography, e.g. preparative RP-HPLC or SPE, if necessary.

Potency

As used herein, the term "potency" or "in vitro potency" is a measure for the ability of a compound to activate the receptors for GLP-1 or glucagon in a cell-based assay. Numerically, it is expressed as the "EC50 value", which is the effective concentration of a compound that induces a half maximal increase of response (e.g. formation of intracellular cAMP) in a dose-response experiment.

Therapeutic Uses & Diagnostic Uses

The compounds of the invention are agonists of the glucagon receptor. Such agonists may at first provide therapeutic benefit to address a clinical need for targeting hypoglycemia.

Accordingly, glucagon receptors agonists of the invention may be used for the treatment of mild to moderate hypoglycemia or in an event of severe hypoglycemia.

The term diagnostic use refers to a use for detection and/or quantification of glucagon receptors in living subjects and relevant tissues.

This includes but is not limited to determination of a receptor occupancy state of a given dose of a therapeutic binding to the glucagon receptor in specific tissues. Glucagon receptors have been identified e.g. in kidney, brain, lymphoid cells of the spleen and thymus, parenchymal cells of the liver and endothelial and Kupffer cells in the liver, heart, adipose tissue, intestinal smooth muscle tissue and endocrine pancreatic cells—expression is particularly high in liver (Watanabe et al, Brazilian journal of Medical and biological research, 1998, 31, 243-256 and references cited therein). Receptor occupancy studies represent an option to identify an optimal dose of said therapeutic agent influencing the glucagon receptor.

Furthermore, a glucagon receptor scintigraphy is particularly applicable in the diagnosis of diseases characterized by increased presence of cells strongly expressing the glucagon receptor, e.g. metastases in glucagonoma e.g. in liver, lymph nodes, mesentery/omentum/peritoneum, lung or adrenals.

A person skilled in the art will be able to select a suitable metal ion for loading depending on the intended imaging technology. This includes, but is not limited to $(Gd-68)^{3+}$ for MRI, $(Cu-64)^{2+}$, $(Ga-68)^{3+}$ $(Al-F-18)^{2+}$ or $(Y-86)^{3+}$ for PET or $(Ga-67)^{3+}$, $(Tc-99m)^{3+}$ or $(In-111)^{3+}$ for SPECT measurements.

The term "therapeutic use" indicates an application of peptides described in the current invention for use in radiotherapy. This involves loading of said peptide with a suitable radionuclide like $(Cu-67)^{2+}$, $(Y-90)^{3+}$, $(In-111)^{3+}$, $(Lu-177)^{3+}$, $(Re-186)^{3+}$ or $(Re-188)^{3+}$, purification and quality control.

A preparation is considered suitable, if a loading efficacy of >98% can be obtained. The radioactive preparation can be injected as a part of an acceptable pharmaceutical composition into a patient. The applied dose is selected by a physician depending on considerations on e.g. the intended use (therapeutic or diagnostic), disease state (benign ort malignant), tumor size and location and loaded radioisotope.

Pharmaceutical Compositions

The term "pharmaceutical composition" indicates a mixture containing ingredients that are compatible when mixed and which may be administered. A pharmaceutical composition may include one or more bioactive molecules. Additionally, the pharmaceutical composition may include carriers, solvents, adjuvants, emollients, expanders, stabilizers and other components, whether these are considered active or inactive ingredients. Guidance for the one skilled in preparing pharmaceutical compositions may be found, for example, in Remington: The Science and Practice of Pharmacy, (20th ed.) ed. A. R. Gennaro A. R., 2000, Lippencott Williams & Wilkins.

The exendin-4 peptide derivatives of the present invention or metal complexes or salts or solvates thereof, are administered in conjunction with an acceptable pharmaceutical carrier, diluent, or excipient as part of a pharmaceutical composition. A "pharmaceutically acceptable carrier" is a carrier which is physiologically acceptable while retaining the therapeutic properties of the substance with which it is administered. Standard acceptable pharmaceutical carriers and their formulations are known to one skilled in the art and described, for example, in Remington: The Science and Practice of Pharmacy, (20th ed.) ed. A. R. Gennaro A. R., 2000, Lippencott Williams & Wilkins. One exemplary pharmaceutically acceptable carrier is physiological saline solution.

Acceptable pharmaceutical carriers or diluents include those used in formulations suitable for oral, rectal, nasal or parenteral (including subcutaneous, intramuscular, intravenous, intradermal, and transdermal) administration. The compounds of the present invention will typically be administered intravenously.

The term "salt" or "pharmaceutically acceptable salt" means salts of the compounds of the invention which are safe and effective for use in mammals. Pharmaceutically acceptable salts may include, but are not limited to, acid addition salts and basic salts. Examples of acid addition salts include chloride, sulfate, hydrogen sulfate, (hydrogen) phosphate, acetate, trifluoroacetate, citrate, tosylate or mesylate salts. Examples of basic salts include salts with inorganic cations, e.g. alkaline or alkaline earth metal salts such as sodium, potassium, magnesium or calcium salts and salts with organic cations such as amine salts. Further examples of pharmaceutically acceptable salts are described in Remington: The Science and Practice of Pharmacy, (20th ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimica Acta, Zurich, Switzerland, and Wiley-VCH, Weinheim, Germany.

The term "solvate" means complexes of the compounds of the invention or salts thereof with solvent molecules, e.g. organic solvent molecules and/or water.

The term "metal complex" means a chelate complex of the compounds of the invention with metal ions (e.g of transition metals) wherein a polydentate (multiple bonded) ligand is a part of the compound that bonds to the metal ion through several of the ligand's atoms; (ligands with 2, 3 or 4 bonds to the metal ion are common).

Pharmaceutical compositions of the invention are those suitable for parenteral (for example subcutaneous, intramuscular, intradermal or intravenous), oral, rectal, topical and peroral (for example sublingual) administration, although the most suitable mode of administration depends in each individual case on the specific use of the bioactive ingredient and on the nature of the compound of formula (I) used in each case. Typically the route of administration for the intended use for the compounds of this invention is intravenous administration.

METHODS

Abbreviations employed are as follows:
2F-Phe 2-Fluorophenylalanine
AA amino acid
cAMP cyclic adenosine monophosphate
Boc tert-butyloxycarbonyl
BOP (benzotriazol-1-yloxy)tris(dimethylamino)phosphonium hexafluorophosphate
tBu tertiary butyl
CT Computer tomography
CTC 2-Chlorotrityl chloride
DIC N,N'-diisopropylcarbodiimide
DIPEA N,N-diisopropylethylamine
DMF dimethyl formamide
EDT ethanedithiol
Fmoc fluorenylmethyloxycarbonyl
GCG Glucagon
GLP-1 Glucagon related peptide 1
HATU 2-(1H-7-azabenzotriazol-1-yl)-1,1,3,3-tetramethyl uronium hexafluorophosphate
HBTU 2-(1H-benzotriazol-1-yl)-1,1,3,3-tetramethyl-uronium hexafluorophosphate
HOBt 1-hydroxybenzotriazole
HPLC High Performance Liquid Chromatography
MRI Magnetic resonance imaging
PEG polyethylene glycol
PET Positron emission tomography
RP-HPLC reversed-phase high performance liquid chromatography
s.c. subcutaneous
SPE Solid phase extraction
SPECT Single photon emission computed tomography
TFA trifluoroacetic acid
Tle tert-Leucine
TRIS Tris(hydroxymethyl)-aminomethan
Trt trityl
Tza 4-Thiazolylalanine
UPLC Ultra High Performance Liquid Chromatography
UV ultraviolet General Synthesis of Peptidic Compounds Materials:

For solid phase peptide synthesis CTC- or preloaded Fmoc-Ser(tBu)-Wang resin or Rink-Amide resin (4-(2',4'-Dimethoxyphenyl-Fmoc-aminomethyl)-phenoxyacetamido-norleucylaminomethyl resin) was used. CTC-resin was purchased from CBL Patras having a loading of 1.4 mmol/g. Fmoc-Cys(Trt)-Wang resin was purchased from Bachem with a loading of 0.5 mmol/g. Rink-Amide resin was purchased from Novabiochem with a loading of 0.23 mmol/g.

Fmoc protected natural amino acids were purchased from Protein Technologies Inc., Senn Chemicals, Merck Biosciences, Novabiochem, Iris Biotech or Bachem. The following standard amino acids were used throughout the syntheses: Fmoc-L-Ala-OH, Fmoc-L-Arg(Pbf)-OH, Fmoc-L-Asn(Trt)-OH, Fmoc-L-Asp(OtBu)-OH, Fmoc-L-Gln(Trt)-OH, Fmoc-L-Glu(OtBu)-OH, Fmoc-Gly-OH, Fmoc-L-His(Trt)-OH, Fmoc-L-Ile-OH, Fmoc-L-Leu-OH, Fmoc-L-Lys(Boc)-OH, Fmoc-L-Phe-OH, Fmoc-L-Pro-OH, Fmoc-L-Ser(tBu)-OH, Fmoc-L-Thr(tBu)-OH, Fmoc-L-Trp(Boc)-OH, Fmoc-L-Tyr(tBu)-OH, Fmoc-L-Val-OH, Fmoc-L-Cys(Trt)-OH.

In addition, the following special amino acids were purchased from the same suppliers as above: Fmoc-L-Tza-OH, Fmoc-Aib-OH, Fmoc-Bal-OH, Fmoc-D-Ser(tBu)-OH, Fmoc-L-Nle-OH, Fmoc-L-2F-Phe-OH, Fmoc-L-Chg-OH, Fmoc-L-Tle-OH The solid phase peptide syntheses were performed on a Prelude Peptide Synthesizer (Protein Technologies Inc) using standard Fmoc chemistry and HBTU/DIPEA activation. DMF was used as the solvent. Deprotection: 20% piperidine/DMF for 2×2.5 min. Washes: 7×DMF. Coupling 2:5:10 200 mM AA/500 mM HBTU/2M DIPEA in DMF 2× for 20 min. Washes: 5×DMF.

All the peptides that had been synthesized were cleaved from the resin with King's cleavage cocktail consisting of 82.5% TFA, 5% phenol, 5% water, 5% thioanisole, 2.5% EDT. The crude peptides were then precipitated in diethyl or diisopropyl ether, centrifuged, and lyophilized. Peptides were analyzed by analytical HPLC and checked by ESI mass spectrometry (see Table 5). Crude peptides were purified by a conventional preparative RP-HPLC purification procedure.

General Preparative HPLC Purification Procedure:

The crude peptides were purified either on an Äkta Purifier System or on a Jasco semiprep HPLC System. Preparative RP-C18-HPLC columns of different sizes and with different flow rates were used depending on the amount of crude peptide to be purified. Acetonitrile+0.1% TFA (B) and water+0.1% TFA (A) were employed as eluents. Product-containing fractions were collected and lyophilized to obtain the purified product, typically as TFA salt.

Stability testing of exendin-4 derivatives:

For stability testing, the target concentration was 0.5 mg/mL pure compound in either a pH 7.3 TRIS buffer (50 mM) containing m-cresol (30 mM), sodium chloride (85 mM) and polysorbate 20 (8 µM) or a pH 4.5 Methionine buffer (20 mM) containing m-Cresol (25 mM) and glycerol (220 mM). The solution was stored for 14 days at 4° C., 25° C. or 40° C. After that time, the solution was analysed by UPLC.

UPLC was performed on a Waters Acquity UPLC H-Class system with a Waters Acquity UPLC BEH130 C18 1.7 µm column (2.1×100 mm) at 40° C. with a gradient elution at a flow rate of 0.5 mL/min and monitored at 215 and 280 nm. The gradients were set up as 10% B to 90% B over 19.2 min and then 90% B for 0.8 min. Buffer A=0.1% formic acid in water and B=0.1% formic acid in acetonitrile.

The "% Purity" after 14 days is defined by the % Relative purity at day 14 in relation to the % Relative purity at t0 following the equation % Purity=[(% Relative purity $t$14)×100)]/% Relative purity $t$0

The % Relative purity at t0 was calculated by dividing the peak area of the peptide at t0 by the sum of all peak areas at t0 following the equation % Relative purity $t$0=[(peak area $t$0)×100]/sum of all peak areas $t$0

Likewise, the % relative purity t14 was calculated by dividing the peak are of the peptide at t14 by the sum of all peak areas at t14 following the equation % Relative purity $t$14=[(peak area t14)×100]/sum of all peak areas $t$14

In analogous way, the % Purity after 7 days can be calculated.

In vitro cellular assays for glucagon receptor efficacy:

Agonism of compounds for the respective receptor was determined by functional assays measuring cAMP response of HEK-293 cell lines stably expressing human GLP-1 or glucagon receptor.

cAMP content of cells was determined using a kit from Cisbio Corp. (cat. no. 62AM4PEC) based on HTRF (Homogenous Time Resolved Fluorescence). For preparation, cells were split into T175 culture flasks and grown overnight to near confluency in medium (DMEM/10% FBS). Medium was then removed and cells washed with PBS lacking calcium and magnesium, followed by proteinase treatment with accutase (Sigma-Aldrich cat. no. A6964). Detached cells were washed and resuspended in assay buffer (1×HBSS; 20 mM HEPES, 0.1% BSA, 2 mM IBMX) and cellular density determined. They were then diluted to 400000 cells/ml and 25 µl-aliquots dispensed into the wells of 96-well plates. For measurement, 25 µl of test compound in assay buffer was added to the wells, followed by incubation for 30 minutes at room temperature. After addition of HTRF reagents diluted in lysis buffer (kit components), the plates were incubated for 1 hr, followed by measurement of the fluorescence ratio at 665/620 nm. In vitro potency of agonists was quantified by determining the concentrations that caused 50% activation of maximal response (EC50).

For exemplary reasons a derivative of native glucacon (SEQ ID NO 2) was synthesized carrying a c-terminal cysteinamide with a VS-DO3A building block coupled to the side chain.

H-S-Q-G-T-F-T-S-D-Y-S-K-Y-L-D-S-R-R-A-Q-D-F-V-Q-W-L-M$^{27}$-N-T-C(VS-DO3A)-NH2

During the synthesis, especially during the conjugation step of the cysteine containing peptide with the VS-DO3A building block, rapid oxidation of methionine in position 27 was observed as well as aggregation, which is already well precedented for the native glucagon sequence. Nevertheless small amounts of the targeted compounds could be obtained. The resulting derivative was tested for Glucagon and GLP-1 receptor activation as in example 5. H-S-Q-G-T-F-T-S-D-Y-S-K-Y-L-D-S-R-R-A-Q-D-F-V-Q-W-L-M$^{27}$-N-T-C(VS-DO3A)-NH2 activated the glucagon receptor with 0.7 pM (EC50 hGLUC R) and the GLP-1 receptor with 16.1 pM (EC50 hGLP-1 R) respectively.

In contrast compounds of the invention do not contain a methionine which can be oxidized during synthesis or storage, are much less prone to aggregation and show much reduced activation of the GLP-1 receptor.

EXAMPLES

The invention is further illustrated by the following examples.

Example 1: Synthesis of VS-DO3A Building Block ([4,10-Bis-carboxymethyl-7-(2-ethenesulfonyl-ethyl)-1,4,7,10tetraaza-cyclododec-1-yl]-acetic Acid)

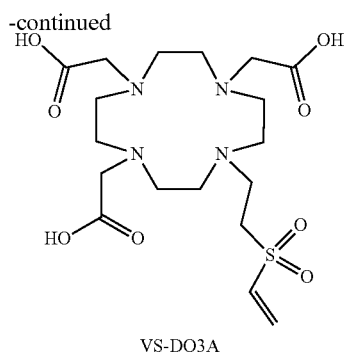

VS-DO3A

To a solution of DO3A-tBu (4,10-Bis-tert-butoxycarbonylmethyl-1,4,7,10tetraaza-cyclododec-1-yl)-acetic acid tert-butyl ester (2.5 g) in DMF (10 mL) was at 0° C. added a solution of divinyl sulfone (5 mL) in DMF/water 1:1 (20 mL). The mixture was allowed to reach room temperature and was stirred for 2 h. The mixture was directly purified by RP chromatography to give VS-DO3A-tBu ([4,10-Bis-tert-butoxycarbonylmethyl-7-(2-ethenesulfonyl-ethyl)-1,4,7,10-tetraaza-cyclododec-1-yl]-acetic acid tert-butyl ester).

A solution of VS-DO3A-tBu in TFA/water 19:1 (75 mL) was stirred at room temperature for 1 day. TFA was carefully evaporated and the remaining solution was freeze-dried to give crude VS-DO3A ([4,10-Bis-carboxymethyl-7-(2-ethene sulfonyl-ethyl)-1,4,7,10tetraaza-cyclododec-1-yl]-acetic acid) which was directly used without further purification.

Example 2: Synthesis of SEQ ID NO: 35

The solid phase synthesis as described in Methods was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.23 mmol/g. The Fmoc-synthesis strategy was applied with HBTU/DIPEA-activation. In position 1 Fmoc-Tza-OH and in position 14 Fmoc-Tle-Nle-OH were used in the solid phase synthesis protocol. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

The purified peptide (53 mg) was then dissolved in pH 7 buffer and the solution was charged with the VS-DO3A building block (14 mg) which was prepared in example 1. The pH was readjusted to pH 7 using pH 10 buffer. The solution was stirred at room temperature for 16 h and was then acidified to pH 4 using acetic acid. The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 3: Synthesis of SEQ ID NO: 36

The peptide synthesized in Example 2 (SEQ. ID 35) was dissolved in acetate buffer pH 4.6 (10 mL) and was charged with gallium(III)-sulfate hydrate (4.8 mg). The mixture was stirred at 80° C. for 15 minutes and was then allowed to reach room temperature. The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 4: Synthesis of SEQ ID NO: 15

The solid phase synthesis as described in Methods was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.23 mmol/g. The Fmoc-synthesis strategy was applied with HBTU/DIPEA-activation. In position 1 Fmoc-Tza-OH, in position 7 Fmoc-Aib-OH and in position 14 Fmoc-Nle-OH were used in the solid phase synthesis protocol. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

The peptide with the free thiol was then dissolved in water/acetonitrile (10/1) before addition of the reducing agent TCEP.HCl (2.5 eq). The pH was adjusted to pH=7 with a 1M NaOH aqueous solution. Finally, the mal-DOTA building block (2.5 eq) was added. The reaction was allowed to stir at room temperature for 10 minutes. Formation of the desired product and total consumption of starting material were confirmed by LCMS.

The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 5: Synthesis of SEQ ID NO: 26

The solid phase synthesis as described in Methods was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.23 mmol/g. The Fmoc-synthesis strategy was applied with HBTU/DIPEA-activation. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA). Finally, the molecular mass of the purified peptide was confirmed by LC-MS.

The peptide was dissolved in water/acetonitrile (10/1) before the addition of DIPEA (60 eq) to reach 9<pH<10. The DOTA building block was then added (1 eq). Successive additions of 0.2 eq of the building block were needed to reach complete conversion of the starting material as judged by LCMS. The crude product was purified via preparative HPLC on a Waters column (Sunfire, Prep C18) using an acetonitrile/water gradient (both buffers with 0.1% TFA). Finally, the molecular mass of the purified peptide was confirmed by LC-MS.

Example 6: Synthesis of SEQ ID NO: 29

The solid phase synthesis as described in Methods was carried out on Novabiochem Rink-Amide resin (4-(2',4'-

Dimethoxyphenyl-Fmoc-aminomethyl)-phenoxyacetamido-norleucylaminomethyl resin), 100-200 mesh, loading of 0.23 mmol/g. The Fmoc-synthesis strategy was applied with HBTU/DIPEA-activation. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA). Finally, the molecular mass of the purified peptide was confirmed by LC-MS.

The peptide was dissolved in 4 mL $Na_2HPO_4$ buffer (pH=9). SPDP-$PEG_8$-NHS ester (1 eq) was added dropwise to the mixture. The reaction mixture was stirred under argon for 10 min at room temperature. Successive additions of 0.2 eq of NHS ester were needed to reach complete conversion as judged by LCMS. TCEP.HCl (5 eq) and mal-NOTA building block (8 eq) were added and the mixture was stirred for 30 minutes.

The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

In an analogous way, the peptides SEQ ID NO: 3-61, 79, 80, 85 and 86 were synthesized, see table 1.

Furthermore, the peptides SEQ ID. NO: 62-78, 81-84 and 87-91 can be synthesized in an analogous way.

TABLE 5 list of synthesized peptides and comparison of calculated vs. found monoisotopic mass.

| SEQ ID | calc. mass | found mass |
|---|---|---|
| 3 | 4905.28 | 4905.27 |
| 4 | 4804.23 | 4804.22 |
| 5 | 4876.25 | 4876.24 |
| 6 | 4843.23 | 4843.30 |
| 7 | 4971.18 | 4971.18 |
| 8 | 4909.13 | 4909.10 |
| 9 | 4870.13 | 4870.13 |
| 10 | 4942.15 | 4942.15 |
| 11 | 4793.25 | 4793.40 |
| 12 | 4859.15 | 4859.30 |
| 13 | 4807.27 | 4807.30 |
| 14 | 4873.17 | 4873.10 |
| 15 | 4869.31 | 4869.31 |
| 16 | 4768.26 | 4768.26 |
| 17 | 4840.29 | 4840.28 |
| 18 | 4935.21 | 4935.21 |
| 19 | 4834.16 | 4834.17 |
| 20 | 4906.19 | 4906.18 |
| 21 | 4909.13 | 4909.20 |
| 22 | 4688.13 | 4688.10 |
| 23 | 4754.03 | 4754.20 |
| 24 | 4825.06 | 4825.20 |
| 25 | 4759.16 | 4759.20 |
| 26 | 4818.31 | 4818.31 |
| 27 | 4884.21 | 4884.21 |
| 28 | 4717.26 | 4717.26 |
| 29 | 5192.46 | 5192.46 |
| 30 | 5258.36 | 5258.36 |
| 31 | 4791.27 | 4791.30 |
| 32 | 4857.18 | 4857.20 |
| 33 | 4887.26 | 4887.30 |
| 34 | 4953.16 | 4953.20 |
| 35 | 4837.28 | 4837.30 |
| 36 | 4903.18 | 4903.25 |
| 37 | 4715.12 | 4715.13 |
| 38 | 4715.17 | 4715.21 |
| 39 | 4730.15 | 4730.19 |
| 40 | 4756.20 | 4756.20 |
| 41 | 4687.13 | 4687.13 |

TABLE 5-continued list of synthesized peptides and comparison of calculated vs. found monoisotopic mass.

| SEQ ID | calc. mass | found mass |
|---|---|---|
| 42 | 4715.17 | 4715.17 |
| 43 | 4940.35 | 4940.40 |
| 44 | 5006.25 | 5006.40 |
| 45 | 4862.34 | 4862.33 |
| 46 | 4928.24 | 4928.24 |
| 47 | 4825.24 | 4825.20 |
| 48 | 4891.14 | 4891.20 |
| 49 | 4887.21 | 4887.20 |
| 50 | 4953.11 | 4953.20 |
| 51 | 4807.30 | 4807.40 |
| 52 | 4873.20 | 4873.20 |
| 53 | 4761.29 | 4761.20 |
| 54 | 4841.25 | 4841.25 |
| 55 | 4907.15 | 4907.15 |
| 56 | 4894.28 | 4894.20 |
| 57 | 4838.27 | 4838.20 |
| 58 | 4815.25 | 4815.30 |
| 59 | 4846.23 | 4846.20 |
| 60 | 4869.24 | 4869.23 |
| 61 | 4935.14 | 4935.16 |
| 79 | 4844.22 | 4844.20 |
| 80 | 4910.12 | 4910.10 |
| 85 | 4887.21 | 4887.20 |
| 86 | 4953.11 | 4953.10 |
| 91 | 4826.27 | 4826.20 |

Example 4: Chemical Stability

Chemical stability of peptidic compounds was assessed as described in Methods. The results are given in Table 5.

TABLE 5

Chemical stability

| Compound | Formulation | Temperature | Purity after 7 days | Purity after 14 days |
|---|---|---|---|---|
| Seq. ID 6 | pH 4.6 | 4° C. | 100 | 99 |
|  |  | 25° C. | 97 | 97 |
|  |  | 40° C. | 92 | 91 |
|  | pH 7.4 | 4° C. | 98 | 96 |
|  |  | 25° C. | 90 | 84 |
|  |  | 40° C. | 64 | 53 |
| Seq. ID 8 | pH 4.6 | 4° C. | 100 | 99 |
|  |  | 25° C. | 99 | 97 |
|  |  | 40° C. | 94 | 84 |
|  | pH 7.4 | 4° C. | 97 | 94 |
|  |  | 25° C. | 81 | 67 |
|  |  | 40° C. | 47 | 33 |
| Seq. ID 13 | pH 4.6 | 4° C. | 99 | 96 |
|  |  | 25° C. | 96 | 94 |
|  |  | 40° C. | 64 | 30 |
|  | pH 7.4 | 4° C. | 96 | 92 |
|  |  | 25° C. | 85 | 76 |
|  |  | 40° C. | 61 | 52 |
| Seq. ID 14 | pH 4.6 | 4° C. | 100 | 94 |
|  |  | 25° C. | 98 | 97 |
|  |  | 40° C. | 93 | 89 |
|  | pH 7.4 | 4° C. | 95 | 93 |
|  |  | 25° C. | 81 | 68 |
|  |  | 40° C. | 47 | 32 |
| Seq. ID 35 | pH 4.6 | 4° C. | 100 | 99 |
|  |  | 25° C. | 97 | 97 |
|  |  | 40° C. | 92 | 91 |
|  | pH 7.4 | 4° C. | 98 | 96 |
|  |  | 25° C. | 90 | 84 |
|  |  | 40° C. | 64 | 53 |
| Seq. ID 36 | pH 4.6 | 4° C. | 100 | 99 |
|  |  | 25° C. | 99 | 97 |
|  |  | 40° C. | 94 | 84 |

TABLE 5-continued

Chemical stability

| Compound | Formulation | Temperature | Purity after 7 days | Purity after 14 days |
|---|---|---|---|---|
| | pH 7.4 | 4° C. | 97 | 94 |
| | | 25° C. | 81 | 67 |
| | | 40° C. | 47 | 33 |
| Seq. ID 49 | pH 4.6 | 4° C. | 100 | 99 |
| | | 25° C. | 97 | 97 |
| | | 40° C. | 92 | 91 |
| | pH 7.4 | 4° C. | 98 | 96 |
| | | 25° C. | 90 | 84 |
| | | 40° C. | 64 | 53 |
| Seq. ID 50 | pH 4.6 | 4° C. | 100 | 99 |
| | | 25° C. | 99 | 97 |
| | | 40° C. | 94 | 84 |
| | pH 7.4 | 4° C. | 97 | 94 |
| | | 25° C. | 81 | 67 |
| | | 40° C. | 47 | 33 |

Example 5: In Vitro Data on GLP-1 and Glucagon Receptor

Potencies of peptidic compounds at the GLP-1 and glucagon receptors were determined by exposing cells expressing human glucagon receptor (hGLUC R), and human GLP-1 receptor (hGLP-1 R) to the listed compounds at increasing concentrations and measuring the formed cAMP as described in Methods.

The results for Exendin-4 derivatives with activity at the human GLP-1 receptor (hGLP-1 R) and the human glucagon receptor (hGLUC R) are shown in Table 6.

TABLE 6

EC50 values of exendin-4 peptide analogues at GLP-1 and Glucagon receptors (indicated in pM)

| SEQ ID NO | EC50 hGLP-1 R [pM] | EC50 hGLUC R [pM] |
|---|---|---|
| 1 | 0.4 | >10000000 |
| 2 | 56.6 | 1.0 |
| 3 | 11100.0 | 1.7 |
| 4 | 3480.0 | 0.8 |
| 5 | 2790.0 | 0.6 |
| 6 | 4960.0 | 0.8 |
| 7 | 7530.0 | 1.2 |
| 8 | 4130.0 | 1.1 |
| 9 | 4200.0 | 1.0 |
| 10 | 4570.0 | 0.9 |
| 11 | 14400.0 | 0.5 |
| 12 | 12900.0 | 0.7 |
| 13 | 143000.0 | 4.8 |
| 14 | 38600.0 | 2.8 |
| 15 | 177000.0 | 5.2 |
| 16 | 9999999.0 | 4.9 |
| 17 | 9999999.0 | 6.7 |
| 18 | 29400.0 | 5.7 |
| 19 | 116000.0 | 4.8 |
| 20 | 168000.0 | 4.7 |
| 21 | 4855.0 | 1.7 |
| 22 | 1010.0 | 6.3 |
| 23 | 725.0 | 5.1 |
| 24 | 8440.0 | 4.3 |
| 25 | 12000.0 | 4.3 |
| 27 | 11500.0 | 2.0 |
| 28 | 11000.0 | 1.6 |
| 29 | 8790.0 | 1.2 |
| 30 | 4010.0 | 0.9 |
| 31 | 9999999.0 | 31.7 |
| 32 | 58700.0 | 52.5 |
| 33 | 29400.0 | 0.9 |
| 34 | 18800.0 | 0.8 |
| 35 | 86700.0 | 2.0 |
| 36 | 65333.3 | 1.7 |
| 37 | 6590.0 | 5.5 |
| 38 | 5070.0 | 4.3 |
| 39 | 14100.0 | 26.6 |
| 40 | 672.0 | 0.3 |
| 41 | 4060.0 | 2.6 |
| 42 | 2210.0 | 0.7 |
| 43 | 44900.0 | 1.4 |
| 44 | 33500.0 | 0.8 |
| 45 | 46500.0 | 1.3 |
| 46 | 37500.0 | 1.3 |
| 47 | 9999999.0 | 79.1 |
| 48 | 297000.0 | 60.1 |
| 49 | 40700.0 | 0.6 |
| 50 | 36900.0 | 0.5 |
| 51 | 9999999.0 | 25.4 |
| 52 | 552000.0 | 17.2 |
| 53 | 31200.0 | 0.9 |
| 54 | 4370.0 | 0.5 |
| 55 | 2610.0 | 0.5 |
| 56 | 10200.0 | 0.6 |
| 57 | 835.0 | 0.5 |
| 58 | 14900.0 | 0.4 |
| 59 | 34200.0 | 1.1 |
| 61 | 13500.0 | 0.5 |
| 79 | 6970.0 | 0.8 |
| 80 | 5130.0 | 0.7 |
| 85 | 146000.0 | 1.0 |
| 86 | 115000.0 | 0.9 |
| 91 | 80.5 | 1.1 |

Example 6: Comparison Testing

A selection of exendin-4 derivatives comprising the artificial amino acid 4-thiazolylalanine in position 1 has been tested in comparison to corresponding compounds that have histidine in position 1. Histidine at position 1 is essential for the activation of the receptor in glucagon but also in many related peptides including GLP-1 and exendin-4. Therefore it is surprising that the artificial amino acid 4-thiazolylalanine leads to a comparable activation of the receptor compared to identical compounds that have the natural histidine at position 1. Furthermore, the activation of the GLP-1 receptor which counterregulates the glucagon effect is surprisingly reduced by the introduction of the artificial amino acid 4-thiazolylalanine. This leads to even more selective glucagon receptor agonists with a higher GCG/GLP-1 activity ratio. The reference pair compounds and the corresponding EC50 values at GLP-1 and Glucagon receptors (indicated in pM) are given in Table 7.

TABLE 7

Comparison of exendin-4 derivatives comprising the artificial amino acid 4-thiazolylalanine in position 1 vs. exendin-4 derivatives having the natural amino acid histidine in position 1. The values for native glucagon (SEQ. ID 2) are also given. EC50 values at GLP-1 and Glucagon receptors are indicated in pM.

| SEQ ID NO | Amino acid in position 1 | EC50 hGLP-1R | EC50 hGlucagon-R | Ratio |
|---|---|---|---|---|
| 2 | His | 56.6 | 1.0 | 57:1 |
| 6 | Tza | 4960.0 | 0.8 | 6200:1 |
| 91 | His | 80.5 | 1.1 | 73:1 |

The invention claimed is:

1. A peptidic compound having the formula (I):

$$\text{Tza-X2-X3-Gly-Thr-Phe-X7-Ser-Asp-X10-Ser-X12-X13-X14-X15-X16-X17-X18-Ala-X20-X21-Phe-Ile-Glu-Trp-Leu-Leu-X28-X29-Gly-Pro-X32-Ser-Gly-Ala-Pro-Pro-Pro-Ser-X40-R^1} \quad (I)$$

X2 represents an amino acid selected from Ser and d-Ser,
X3 represents an amino acid selected from Gln and His,
X7 represents an amino acid selected from Thr and Aib,
X10 represents an amino acid residue selected from Tyr, Leu, Val, Ile, Phe, Phenylglycine, Thr, 2-Fluorophenylalanine, Cyclohexylglycine and tert-Leucine,
X12 represents an amino acid selected from Lys, Arg and Cys(VS-DO3A),
X13 represents an amino acid selected from Gln, Tyr and Cys(VS-DO3A),
X14 represents an amino acid residue selected from Leu, Nle and Cys(VS-DO3A),
X15 represents an amino acid selected from Glu and Asp,
X16 represents an amino acid selected from Ser, Glu, Aib and Cys(VS-DO3A),
X17 represents an amino acid selected from Arg, Gln, Lys, Ala and Cys(VS-DO3A),
X18 represents an amino acid selected from Arg, Lys and Ala,
X20 represents an amino acid selected from Gln, Glu, Aib, Lys and Cys(VS-DO3A), if X16 is Glu and X20 is Lys, the sidechains of X16 and X20 optionally form a cyclic ring via a lactam,
X21 represents an amino acid residue selected from Asp and Glu,
X28 represents an amino acid selected from Ala and β-Ala,
X29 represents an amino acid residue selected from Gly and Thr,
X32 represents an amino acid selected from Glu and Ser,
X40 represents an amino acid selected from Cys(VS-DO3A), Cys(VS-NO2A), Cys(mal-DOTA), Cys(mal-NOTA), Cys(mal-NODAGA), Lys(DOTA), Lys(NOTA), Lys(PEG-DOTA) and Lys(VS-DO3A),
wherein X40 is absent if one of the amino acids X12, X13, X14, X16, X17 or X20 is Cys(VS-DO3A),
wherein DOTA, NOTA, DO3A, NO2A or NODAGA are optionally loaded with a metal ion selected from $Gd^{3+}$, $Ga^{3+}$, $Cu^{2+}$, $(Al-F)^{2+}$, $Tc^{3+}$, $In^{3+}$, $Lu^{3+}$ and $Re^{3+}$,
$R^1$ represents OH or $NH_2$;
or a metal complex or a salt or a solvate thereof.

2. A compound of formula (I) according to claim 1, wherein
X2 represents an amino acid selected from Ser and d-Ser,
X3 is Gln,
X7 represents an amino acid selected from Thr and Aib,
X10 represents an amino acid residue selected from Tyr, Leu, Ile,
X12 is Lys,
X13 is Gln, X14 represents an amino acid residue selected from Leu and Nle, X15 represents an amino acid selected from Glu and Asp, X16 represents an amino acid selected from Ser and Glu, X17 represents an amino acid selected from Arg and Gln, X18 is Arg, X20 represents an amino acid selected from Gln and Lys, if X16 is Glu and X20 is Lys, the sidechains of X16 and X20 optionally form a cyclic ring via a lactam, X21 represents an amino acid residue selected from Asp and Glu, X28 is Ala, X29 represents an amino acid residue selected from Gly and Thr, X32 is Glu, X40 is Cys(VS-DO3A), wherein DO3A, is optionally loaded with a metal ion selected from $Ga^{3+}$, $Cu^{2+}$, $(Al-F)^{2+}$, $Y^{3+}$, $Tc^{3+}$, $In^{3+}$, $Lu^{3+}$ and $Re^{3+}$, $R^1$ represents OH or $NH_2$;

or a metal complex or a salt or a solvate thereof.

3. A compound of formula (I) according to claim 1, selected from the compounds of SEQ ID NO: 3-90 as well as a metal complex, salts or solvates thereof.

4. A compound of formula (I) according to claim 1, selected from the compounds of SEQ ID NO: 6, 8, 13, 14, 35, 36, 49, 50, 60, 61, 79, 80, 85 and 86 as well as a metal complex, salts or solvates thereof.

5. A compound of formula (I) according to claim 1, wherein DOTA, NOTA, DO3A, NO2A or NODAGA is loaded with a metal ion $Ga^{3+}$.

6. A compound of formula (I) according to claim 1, wherein DOTA, NOTA, DO3A, NO2A or NODAGA is loaded with a metal ion $Gd^{3+}$.

7. A compound of formula (I) according to claim 1, wherein DOTA, NOTA, DO3A, NO2A or NODAGA is loaded with a metal radionucleotide ion selected from $(Cu-64)^{2+}$, $(Ga-68)^{3+}$, $(Al-F-18)^{2+}$, and $(Y-86)^{3+}$.

8. A compound of formula (I) according to claim 1, wherein DOTA, NOTA, DO3A, NO2A or NODAGA is loaded with a metal radionucleotide ion selected from $(Ga-67)^{3+}$, $(Tc-99m)^{3+}$, and $(In-111)^{3+}$.

9. A compound of formula (I) according to claim 1, wherein DOTA, NOTA, DO3A, NO2A or NODAGA is loaded with a metal radionucleotide ion selected from $(Cu-67)^{2+}$, $(Y-90)^{3+}$, $(In-111)^{3+}$, $(Lu-177)^{3+}$, $(Re-186)^{3+}$ and $(Re-188)^{3+}$.

10. A pharmaceutical composition comprising at least one compound according to claim 1 or a physiologically acceptable salt or solvate thereof.

11. A method for treating neuroendocrine tumors characterized by increased expression of a glucagon receptor in a patient suffering therefrom, the method comprising administering to the patient an effective amount of the pharmaceutical composition according to claim 10.

12. A method for visualizing a glucagon receptor in living subjects or relevant tissues, the method comprising:
    administering an effective amount of the compound according to claim 1 to the living subjects or relevant tissues; and
    visualizing the glucagon receptor in the living subjects or relevant tissues.

13. A method for treating neuroendocrine tumors characterized by increased expression of a glucagon receptor in a patient suffering therefrom, the method comprising administering to the patient an effective amount of the compound according to claim 1, wherein the patient is a human.

14. A method for visualizing a glucagon receptor in living subjects or relevant tissues, the method comprising:
    administering an effective amount of the compound according to claim 6 to the living subjects or relevant tissues; and
    visualizing the glucagon receptor in the living subjects or relevant tissues by magnetic resonance imaging, MRI.

15. A method for visualizing a glucagon receptor in living subjects or relevant tissues, the method comprising:
    administering an effective amount of the compound according to claim 7 to the living subjects or relevant tissues; and
    visualizing the glucagon receptor in the living subjects or relevant tissues by positron emission tomography, PET.

16. A method for visualizing a glucagon receptor in living subjects or relevant tissues, the method comprising:
    administering an effective amount of the compound according to claim 8 to the living subjects or relevant tissues; and
    visualizing the glucagon receptor in the living subjects or relevant tissues by single photon emission computed tomography, SPECT.

17. A method for conducting radiotherapy in a patient suffering from a disease or a condition involving a glucagon receptor, the method comprising administering to the patient an effective amount of the compound according to claim 9.

18. A method for increasing blood glucose levels in a patient suffering from a disease or a condition involving a glucagon receptor, the method comprising administering to the patient, an effective amount of the compound according to claim 1, optionally wherein the treatment is an adjunctive therapy with insulin.

19. A method for treating hypoglycemia in a patient, the method comprising administering to the patient an effective amount of at least one compound of formula (I) according to claim 1.

20. The method according to claim 19 which wherein the at least one compound of formula (I) according to claim 1 is administered parenterally.

* * * * *